US008637672B2

(12) United States Patent
Flynn et al.

(10) Patent No.: US 8,637,672 B2
(45) Date of Patent: Jan. 28, 2014

(54) CYCLOPROPYL DICARBOXAMIDES AND ANALOGS EXHIBITING ANTI-CANCER AND ANTI-PROLIFERATIVE ACTIVITIES

(75) Inventors: Daniel L. Flynn, Lawrence, KS (US); Michael D. Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 13/559,170

(22) Filed: Jul. 26, 2012

(65) Prior Publication Data

US 2012/0322834 A1 Dec. 20, 2012

Related U.S. Application Data

(63) Continuation of application No. 13/098,243, filed on Apr. 29, 2011.

(60) Provisional application No. 61/329,548, filed on Apr. 29, 2010.

(51) Int. Cl.
| C07D 213/30 | (2006.01) |
| C07D 213/28 | (2006.01) |
| C07D 401/12 | (2006.01) |
| C07D 401/14 | (2006.01) |
| A61K 31/44  | (2006.01) |
| A61P 35/00  | (2006.01) |

(52) U.S. Cl.
USPC .......................................... 546/296; 514/335

(58) Field of Classification Search
USPC .......................................... 546/296; 514/335
See application file for complete search history.

(56) References Cited

U.S. PATENT DOCUMENTS

| 7,790,885 B2 | 9/2010 | Nagai et al. |
| 7,855,290 B2 | 12/2010 | Matsushima et al. |
| 2005/0245530 A1 | 11/2005 | Borzilleri et al. |
| 2005/0277652 A1 | 12/2005 | Matsushima et al. |
| 2007/0270421 A1 | 11/2007 | Matsushima et al. |
| 2008/0255155 A1 | 10/2008 | Raeppel et al. |
| 2008/0318924 A1 | 12/2008 | Matsushima et al. |
| 2008/0319188 A1 | 12/2008 | Matsushima et al. |
| 2009/0227556 A1 | 9/2009 | Obaishi |
| 2010/0081805 A1 | 4/2010 | Deschamps et al. |
| 2010/0311972 A1 | 12/2010 | Nagai |

FOREIGN PATENT DOCUMENTS

| EP | 1889836 A1 | 2/2008 |
| EP | 2119706 A1 | 11/2009 |
| JP | 2010178651 A | 8/2010 |
| WO | WO 2007/023768 A1 | 3/2007 |
| WO | WO 2008/023698 A1 | 2/2008 |
| WO | WO 2008/026577 A1 | 3/2008 |
| WO | WO 2008/063202 A2 | 5/2008 |
| WO | WO 2008/102870 A1 | 8/2008 |
| WO | WO 2009/033084 A1 | 3/2009 |
| WO | WO 2009/077874 A2 | 6/2009 |
| WO | WO 2009/104520 A1 | 8/2009 |
| WO | WO 2010/051373 A1 | 5/2010 |
| WO | WO 2010/064300 A1 | 10/2010 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Mass, R. D., Int. J. Radiation Oncology Bio. Phys. vol. 58(3): 932-940, 2004.*
Fabbro et al. Pharmacology & therapeutics 93, 79-98, 2002.*
Liu et al. Expert Opin. Investig. Drugs (2011) 20(9):1225-1241.*
Aklilu, F. et al., "Increased PTHRP Production by a Tyrosine Kinase Oncogene, Tpr-Met: Role of the Ras Signaling Pathway". American Journal of Physiology, Endocrinology and Metabolism. vol. 271, No. 2, Aug. 1996, pp. E277-E283.
Yin, J. and Buchwald, S.L., "Palladium Catalyzed Intermolecular Coupling of Aryl Halides and Amides". Organic Letters. vol. 2, No. 8, Mar. 2000, pp. 1101-1104.
Ma, P.C. et al., "C-Met: Structure, Functions and Potential for Therapeutic Inhibition". Cancer and Metastasis Reviews. vol. 22, Issue 4, Dec. 2003, pp. 309-325.
Ma, P.C. et al., "C-Met Mutational Analysis in Small Cell Lung Cancer: Novel Juxtamembrane Domain Mutations Regulating Cytoskeletal Functions". Cancer Research. vol. 63, Oct. 2003, pp. 6272-6281.
Moss, G.P., "Basic Terminology of Stereochemistry. Pure and Applied Chemistry". vol. 68, No. 12, 1996, pp. 2193-2222.
Muller, P., "Glossary of Terms Used in Physical Organic Chemistry". Pure and Applied Chemistry. vol. 66, No. 5, 1994, pp. 1077-1184.
Nakopoulou, L. et al., "C-Met Tyrosine Kinase Receptor Expression is Associated with Abnormal β-Catenin Expression and Favourable Prognostic Factors in Invasive Breast Carcinoma". Histopathology, vol. 36, No. 4, 2000, pp. 313-325.
Park, M. et al., "Mechanism of *Met*Oncogene Activation". Cell. vol. 45, Jun. 1986, pp. 895-904.
Ponzetto, C. et al., "A Novel Recognition Motif for Phosphatidylinositol 3-Kinase Binding Mediates its Association with the Hepatocyte Growth Factor/Scatter Factor Receptor". Molecular and Cell Biology. vol. 13, No. 8, Aug. 1993, pp. 4600-4608.

(Continued)

*Primary Examiner* — Venkataraman Balasubramanian
(74) *Attorney, Agent, or Firm* — Cooley LLP

(57) ABSTRACT

The disclosed compounds are useful in the treatment of mammalian cancers and especially human cancers. Compounds, pharmaceutical compositions, and methods of Formula I are disclosed:

Formula I

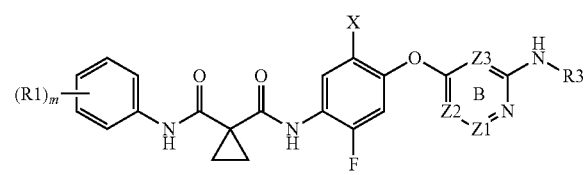

or a pharmaceutically acceptable salt, hydrate, solvate, enantiomer, stereoisomer, or tautomer thereof.

19 Claims, No Drawings

(56) References Cited

OTHER PUBLICATIONS

Schindler, T. et al., "Structural Mechanism for STi-571 Inhibition of Abelson Tyrosine Kinase". Science. vol. 289, No. 5486, Sep. 2000, pp. 1938-1942.

Schmidt, L. et al., "Germline and Somatic Mutations in the Tyrosine Kinase Domain of the *MET*Proto-Oncogene in Papillary Renal Carcinomas". Nature Genetics. vol. 16, May 1997, pp. 68-73.

Schmidt, L. et al., "Novel Mutations of the MET Proto-Oncogene in Papillary Renal Carcinomas". Oncogene. vol. 18, 1999, pp. 2343-2350.

Yu, J. et al., "Frequency of TPR-MET Rearrangement in Patients with Gastric Carcinoma and in First-Degree Relatives". Cancer. vol. 88, No. 8, Apr. 2000, pp. 1801-1806.

Zhen, Z. et al., "Structural and Functional Domains Critical for Constitutive Activation of the HGF-Receptor (*MET*)". Oncogene. vol. 9, No. 6, 1994, pp. 1691-1697.

Stahl, P.H., Wermuth, C.G. Eds., "Handbook of Pharmaceutical Salts: Properties, Selection and Use". VHCA, Verlag Helvetica Chimica Acta, Zurich, Switzerland, Wiley-VCH Verlag GmbH & Co. KgaA, Weinheim, Germany, 2002.

March, J., "Advanced Organic Chemistry: Reactions, Mechanisms and Structure". $4^{th}$ Ed. John Wiley & Sons. 1992, pp. 69-74.

Gregoire, "International Search Report". 3 pages, International Patent Appl. No. PCT/US2011/034556, European Patent Office (mailed Jul. 26, 2011).

Gregoire, "Written Opinions of the International Searching Authority". 6 pages, International Patent Appl. No. PCT/US2011/034556, European Patent Office (mailed Jul. 26, 2011).

\* cited by examiner

CYCLOPROPYL DICARBOXAMIDES AND ANALOGS EXHIBITING ANTI-CANCER AND ANTI-PROLIFERATIVE ACTIVITIES

CROSS-REFERENCE TO RELATED APPLICATIONS

This application is a continuation application of U.S. patent application Ser. No. 13/098,243, filed on Apr. 29, 2011, which in turn claims the benefit of U.S. Provisional Patent Application No. 61/329,548, now abandoned, filed Apr. 29, 2010, entitled "CYCLOPROPYL DICARBOXAMIDES AND ANALOGS EXHIBITING ANTI-CANCER AND ANTI-PROLIFERATIVE ACTIVITIES, each of which is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_043_03US_SeqList_ST25.txt, date recorded: Aug. 24, 2012, file size 13 kilobytes).

FIELD

The present invention relates to kinase inhibitors exhibiting novel and unexpected properties useful for the treatment of various diseases including hyperproliferative diseases and cancer. More particularly, the invention is concerned with such compounds, methods of treating diseases, and methods of synthesis of the compounds. Preferably, the compounds are useful for the modulation of activity of c-MET kinase, c-MET kinase polymorphs, c-MET kinase mutants, or c-MET kinase fusion proteins in the treatment of mammalian diseases, and in particular human hyperproliferative diseases and human cancers. In some embodiments, compounds disclosed herein exhibit unexpected selectivity for modulation of c-MET kinase activity.

BACKGROUND OF THE INVENTION c-MET is a receptor tyrosine kinase (RTK) located on chromosome 7p and activated via its natural ligand hepatocyte growth factor. c-MET is found mutated in a variety of solid tumors (Ma, P. C. et al. *Cancer Metastasis* (2003) 22: 309). Mutations in the tyrosine kinase domain are associated with hereditary papillary renal cell carcinomas (Schmidt, L. et al. *Nat. Genet.* (1997)16: 68; Schmidt, L. et al. *Oncogene* (1999) 18: 2343), whereas mutations in the sema and juxtamembrane domains are often found in small cell lung cancers (Ma, P. C. et al. *Cancer Res.* (2003) 63: 6272). Many activating mutations are also found in breast cancers (Nakopoulou, et al. *Histopath.* (2000) 36(4): 313). The panoply of tumor types for which c-MET mediated growth has been implicated suggests this is a target ideally suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N'-nitro-N-nitrosoguanidine (Park, M. et al. *Cell* (1986) 45: 895). The TPR-MET fusion oncoprotein is the result of a chromosomal translocation, placing the TPR3 locus on chromosome 1 upstream of a portion of the c-MET gene on chromosome 7 encoding only for the cytoplasmic region. Studies suggest that TPR-MET is detectable in experimental cancers (e.g., Yu, J. et al. *Cancer* (2000) 88: 1801). Dimerization of the $M_r$ 65,000 TPR-MET oncoprotein through a leucine zipper motif encoded by TPR leads to constitutive activation of the c-MET kinase (Zhen, Z. et al. *Oncogene* (1994) 9: 1691). TPR-MET activates wild-type c-MET RTK and can activate crucial cellular growth pathways, including the Ras pathway (Aklilu, F. et al. *Am. J. Physiol.* (1996)271: E277) and the phosphatidylinositol 3-kinase(PI3K)/AKT pathway (Ponzetto, C. et al. *Mol. Cell. Biol.* (1993) 13: 4600). Conversely, in contrast to c-MET RTK, TPR-MET is ligand independent, lacks the CBL-like SH2 domain binding site in the juxtamembrane region in c-MET, and is mainly cytoplasmic. c-MET immunohistochemical expression seems to be associated with abnormal β-catenin expression, a hallmark feature of epithelial to mesenchymal transition (EMT) and provides good prognostic and predictive factors in breast cancer patients.

In human therapeutics, it is desirable to provide small molecule inhibitors of a protein target within in a protein family which do not cross-inhibit closely related protein family members. These closely related protein family members are often referred to as 'off-targets', to distinguish them from the essential target of interest referred to as the 'on target' of the inhibitor. A small molecule which inhibits multiple protein family members, while being potent against the target of interest, can be limited in its utility as a human therapeutic due to unintended side effects and toxicities introduced due to the consequences of inhibition of these 'off targets.'

Protein kinases constitute an important therapeutic protein family. There are approximately 518 human protein kinases. While inhibition of a desired kinase 'on target' is desirable for a human therapeutic, it is also desirable in many cases to provide a selective kinase inhibitor which does not substantially inhibit other kinase 'off targets' from within this protein family. Monoclonal antibodies are one approach to providing specific inhibitors to a specific kinase without inhibiting 'off targets.' Achieving this level of selectivity with small molecule inhibitors, however, is not as easily achievable nor as straightforward. Accordingly, there is a need for kinase inhibitors that are selective for a particular protein kinase. It is theorized that an unexpected increase in potency for c-MET kinase inhibition or an unexpected increase in selective c-MET inhibition relative to other kinases is observed for one or more of the embodiments disclosed herein.

SUMMARY

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms, aberrant fusion protein forms, and mutant forms of c-MET kinase.

Specifically, compounds of Formula I are disclosed which find utility in the treatment of diseases as described above.

Formula I

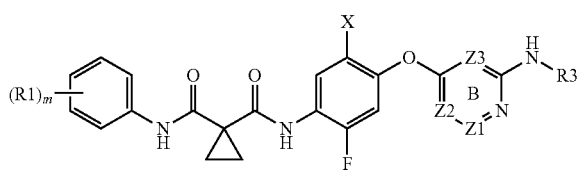

In Formula I, X and F are regiochemically oriented with respect to each other in a mutual para-orientation; X is halogen or C1-C6 alkyl; and R3 is a non-hydrogen moiety regiochemically oriented ortho- to the B ring nitrogen. Compounds described herein exhibit unexpected potency for c-MET kinase inhibition and/or an unexpected increase in selective c-MET kinase inhibition relative to other kinases, particularly in comparison to other purported c-MET kinase inhibitors.

In one aspect, compounds of the Formula I are described:

Formula I

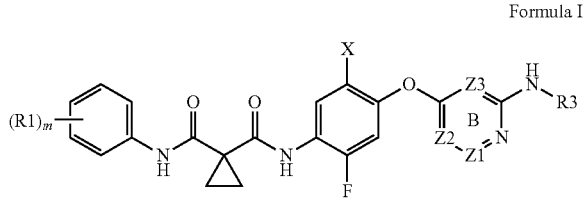

and pharmaceutically acceptable salts, hydrates, solvates, enantiomers, stereoisomers, and tautomers thereof;
wherein
X is halogen;
Z1 and Z2 are independently and individually CR2 or N;
Z3 is CH or N;
with the proviso that ring B is not a tetrazine;
each R1 is independently and individually halogen, H, C1-C6 alkyl, branched C3-C7 alkyl, C3-C7 cycloalkyl, or —CN;
each R2 is individually and independently H, halogen, C1-C6 alkyl, or cyano;
R3 is —C(O)R4, —C(O)—C6-C10-aryl, —C(O)—C4-C6-heterocyclyl, or —C(O)—C5-C6-heteroaryl, wherein
  aryl is phenyl, naphthyl, tetrahydronaphthyl, indenyl or indanyl; and
  with the proviso that when R3 is —C(O)—C4-C6-heterocyclyl, the heterocyclyl does not have a N bonding hand to —C(O);
R4 is C1-C7 alkyl, C3-C8 cycloalkyl, —(CH$_2$)$_p$—CN, —(CH$_2$)$_p$—OR6, —(CH$_2$)$_p$—NR6(R7), —(CH$_2$)$_p$—SO$_2$—C1-C6-alkyl, —(CH$_2$)$_p$—C6-C10-aryl, —(CH$_2$)$_p$—C5-C6-heteroaryl, or —(CH$_2$)$_p$—C4-C6-heterocyclyl, wherein
  each alkyl or alkylene is optionally substituted with one or two C1-C6 alkyl; and
  aryl is phenyl, naphthyl, tetrahydronaphthyl, indenyl or indanyl;
each R6 and R7 is individually and independently H, C1-C6 alkyl, or C3-C8 branched alkyl;
each cycloalkyl, aryl, heteroaryl and heterocyclyl is independently substituted with —(R25)$_m$;
each R25 is individually and independently C1-C6 alkyl, branched C3-C8 alkyl, halogen, —(CH$_2$)$_m$—CN, —(CH$_2$)$_m$—OR6, —(CH$_2$)$_m$—NR6(R7), —(CH$_2$)$_m$—SO$_2$—C1-C6-alkyl, —(CH$_2$)$_m$—C(O)NR6(R7), —(CH$_2$)$_m$—C(O)—C4-C6-heterocyclyl, or —(CH$_2$)$_m$—C4-C6-heterocyclyl, wherein each alkyl or alkylene is optionally substituted with one or two C1-C6 alkyl;
each m is individually and independently 0, 1, 2, or 3; and
p is 1, 2, or 3.

In some embodiments of the compound of Formula I, Z1 and Z2 are CR2, and Z3 is CH.

In certain embodiments, the compound is a compound of Formula Ic,

Formula Ic

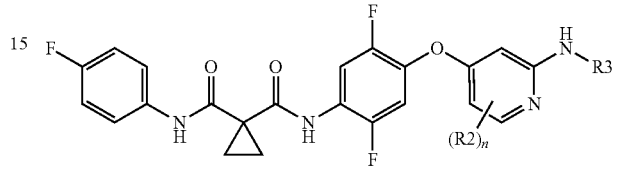

or a pharmaceutically acceptable salt, hydrate, solvate, enantiomer, stereoisomer, or tautomer thereof, and
wherein n is 0, 1, or 2.

In certain embodiments of the compound of Formula Ic, R3 is —C(O)R4.

In other embodiments of the compound of Formula Ic, R3 is —C(O)R4 and R4 is C1-C7 alkyl, C3-C8 cycloalkyl, —(CH$_2$)$_p$—CN, —(CH$_2$)$_p$—OR6, —(CH$_2$)$_p$—NR6(R7), —(CH$_2$)$_p$—SO$_2$—C1-C6-alkyl, or —(CH$_2$)$_p$—C4-C6-heterocyclyl, and wherein each alkyl or alkylene is optionally substituted with one or two C1-C6 alkyl.

In some embodiments of the compound of Formula Ic, R3 is —C(O)R4 and R4 is C1-C7 alkyl or C3-C8 cycloalkyl, and wherein each alkyl or alkylene is optionally substituted with one or two C1-C6 alkyl.

In some embodiments of the compound of Formula Ic, R3 is —C(O)—C6-C10-aryl, —C(O)—C4-C6-heterocyclyl, or —C(O)—C5-C6-heteroaryl.

In some embodiments of the compound of Formula I, Z1 and Z2 are CR2, and Z3 is N.

In certain embodiments, the compound of Formula I is a compound of Formula If,

Formula If

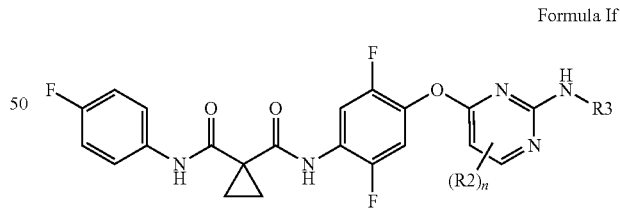

or a pharmaceutically acceptable salt, hydrate, solvate, enantiomer, stereoisomer, or tautomer thereof, and
wherein
n is 0, 1, or 2.

In certain embodiments of the compound of Formula If, R3 is —C(O)R4.

In other embodiments of the compound of Formula If, R3 is —C(O)—C6-C10-aryl, —C(O)—C4-C6-heterocyclyl, or —C(O)—C5-C6-heteroaryl.

In some embodiments of the compound of Formula I, Z1 is CR2, Z2 is N, and Z3 is CH.

In certain embodiments, the compound of Formula I is a compound of Formula Ij,

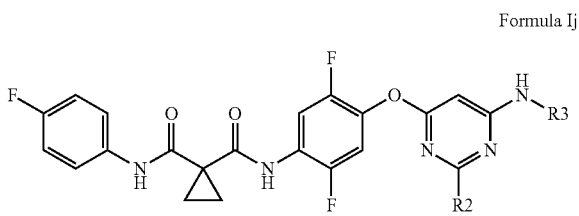

Formula Ij or a pharmaceutically acceptable salt, hydrate, solvate, enantiomer, stereoisomer, or tautomer thereof.

In certain embodiments of the compound of Formula Ij, R3 is —C(O)R4.

In other embodiments of the compound of Formula Ij, R3 is —C(O)—C6-C10-aryl, —C(O)—C4-C6-heterocyclyl, or —C(O)—C5-C6-heteroaryl.

In some embodiments of the compound of Formula I, Z1 is CR2, and Z2 and Z3 are N.

In certain embodiments, the compound of Formula I is a compound of Formula Im,

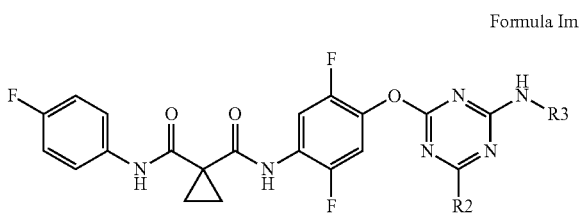

Formula Im or a pharmaceutically acceptable salt, hydrate, solvate, enantiomer, stereoisomer, or tautomer thereof.

In some embodiments of the compound of Formula Im, R3 is —C(O)R4.

In other embodiments of the compound of Formula Im, R3 is —C(O)—C6-C10-aryl, —C(O)—C4-C6-heterocyclyl, or —C(O)—C5-C6-heteroaryl.

In one embodiment, the present invention is directed to a compound selected from the group consisting of N-(4-(2-acetamidopyridin-4-yloxy)-2,5-difluorophenyl)-N'-(4-fluorophenyl)cyclopropane-1,1-dicarboxamide, N-(4-(2-acetamidopyridin-4-yloxy)-5-chloro-2-fluorophenyl)-N'-(4-fluorophenyl)cyclopropane-1,1-dicarboxamide, N-(4-(2-acetamidopyridin-4-yloxy)-2,5-difluorophenyl)-N'-phenylcyclopropane-1,1-dicarboxamide, N-(4-(2-(2-(dimethylamino)acetamido)pyridin-4-yloxy)-2,5-difluorophenyl)-N'-(4-fluorophenyl)cyclopropane-1,1-dicarboxamide, N-(4-(2-acetamidopyrimidin-4-yloxy)-2,5-difluorophenyl)-N'-(4-fluorophenyl)cyclopropane-1,1-dicarboxamide, N-(4-(2-(cyclopropanecarboxamido)pyridin-4-yloxy)-2,5-difluorophenyl)-N'-(4-fluorophenyl)cyclopropane-1,1-dicarboxamide, N-(2,5-difluoro-4-(2-propionamidopyridin-4-yloxy)phenyl)-N'-(4-fluorophenyl)cyclopropane-1,1-dicarboxamide, N-(2,5-difluoro-4-((2-(2-methoxyacetamido)pyridin-4-yl)oxy)phenyl)-N'-(4-fluorophenyl)cyclopropane-1,1-dicarboxamide, N-(2,5-difluoro-4-(2-isobutyramidopyridin-4-yloxy)phenyl)-N'-(4-fluorophenyl)cyclopropane-1,1-dicarboxamide, N-(4-(2-(2-cyanoacetamido)pyridin-4-yloxy)-2,5-difluorophenyl)-N'-(4-fluorophenyl)cyclopropane-1,1-dicarboxamide, N-(4-(2-(azetidine-3-carboxamido)pyridin-4-yloxy)-2,5-difluorophenyl)-N'-(4-fluorophenyl)cyclopropane-1,1-dicarboxamide, N-(4-(2-(cyclobutanecarboxamido)pyridin-4-yloxy)-2,5-difluorophenyl)-N'-(4-fluorophenyl)cyclopropane-1,1-dicarboxamide, (R)—N-(2,5-difluoro-4-((2-(2-methoxypropanamido)pyridin-4-yl)oxy)phenyl)-N'-(4-fluorophenyl)cyclopropane-1,1-dicarboxamide, R)—N-(2,5-difluoro-4-((2-(2-hydroxypropanamido)pyridin-4-yl)oxy)phenyl)-N'-(4-fluorophenyl)cyclopropane-1,1-dicarboxamide, N-(2,5-difluoro-4-((2-pivalamidopyridin-4-yl)oxy)phenyl)-N'-(4-fluorophenyl)cyclopropane-1,1-dicarboxamide, (S)—N-(2,5-difluoro-4-((2-(2-methoxypropanamido)pyridin-4-yl)oxy)phenyl)-N-(4-fluorophenyl)cyclopropane-1,1-dicarboxamide, (S)-1-((4-(2,5-difluoro-4-(1-((4-fluorophenyl)carbamoyl)cyclopropanecarboxamido)phenoxy)pyridin-2-yl)amino)-1-oxopropan-2-yl acetate, N-(2,5-difluoro-4-((2-(2-fluoro-2-methylpropanamido)pyridin-4-yl)oxy)phenyl)-N'-(4-fluorophenyl)cyclopropane-1,1-dicarboxamide and pharmaceutically acceptable salts, solvates, hydrates and tautomers thereof.

In another embodiment, the present invention is directed to a compound selected from the group consisting of N-(4-(2-(cyclopropanecarboxamido)pyridin-4-yloxy)-2,5-difluorophenyl)-N'-(4-fluorophenyl)cyclopropane-1,1-dicarboxamide, N-(2,5-difluoro-4-(2-propionamidopyridin-4-yloxy)phenyl)-N'-(4-fluorophenyl)cyclopropane-1,1-dicarboxamide, N-(2,5-difluoro-4-(2-isobutyramidopyridin-4-yloxy)phenyl)-N'-(4-fluorophenyl)cyclopropane-1,1-dicarboxamide, N-(4-(2-acetamidopyridin-4-yloxy)-2,5-difluorophenyl)-N'-(4-fluorophenyl)cyclopropane-1,1-dicarboxamide.

In some embodiments, the present invention comprises a method of treating mammalian disease wherein the disease etiology or progression is at least partially mediated by a kinase activity, wherein the kinase is a wildtype form, a mutant oncogenic form, an aberrant fusion protein form or a polymorph, the method comprising administering to a mammal in need thereof an effective amount of a compound of Formula I as described herein.

In certain embodiments, the disease etiology or progression is at least partially mediated by the kinase activity of c-MET, mutant oncogenic forms, aberrant fusion proteins, or polymorphs thereof.

In some embodiments, the invention is directed to a pharmaceutical composition, comprising a compound of Formula I as described herein and a pharmaceutically acceptable carrier.

In certain embodiments, the pharmaceutical composition further comprises an additive selected from adjuvants, excipients, diluents, or stabilizers.

In other embodiments the present invention is directed to a method of treating cancer, gastrointestinal stromal tumors, hyperproliferative diseases, metabolic diseases, neurodegenerative diseases, or diseases characterized by angiogenesis, such as solid tumors, melanomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary, mastocytosis, or mast cell leukemia, the method comprising administering to a patient in need thereof an effective amount of a compound of Formula I as described herein.

In some embodiments, the compound is administered orally, parenterally, by inhalation, or subcutaneously.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof, as well as crystalline polymorphic forms of the disclosed compounds and any and all possible isomers, stereoisomers, enantiomers, diastereomers, tautomers, pharmaceutically acceptable salts, and solvates thereof. Thus, the terms "compound" and "compounds" as used in this disclosure refer to the compounds of this disclosure and any and all possible isomers, stereoisomers, enantiomers, diastereomers, tautomers, pharmaceutically acceptable salts, and solvates, and crystalline polymorphs thereof.

Definitions

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH$_2$—, —CH$_2$CH$_2$—, and —CH$_2$CH$_2$CH$_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom to —C(O) to form an amide, carbamate, or urea. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized it electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom to —C(O) to form an amide, carbamate, or urea. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine; meglumine (N-methylglucamine) and procaine.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically acceptable salts of free acid-containing compounds disclosed herein include metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering" or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" as used herein with regard to a subject, refers to improving at least one symptom of the subject's disorder. Treating can be curing, improving, or at least partially ameliorating the disorder.

The term "hydrate" as used herein refers to a compound disclosed herein which is associated with water in the molecular form, i.e., in which the H—OH bond is not split, and may be represented, for example, by the formula R.H$_2$O, where R is a compound disclosed herein. A given compound may form more than one hydrate including, for example, monohydrates (R.H₂O), dihydrates (R.2H₂O), trihydrates (R.3H₂O), and the like.

The term "solvate" as used herein refers to a compound disclosed herein which is associated with solvent in the molecular form, i.e., in which the solvent is coordinatively bound, and may be represented, for example, by the formula R.(solvent), where R is a compound disclosed herein. A given compound may form more than one solvate including, for example, monosolvates (R.(solvent)) or polysolvates (R.n (solvent)) wherein n is an integer greater than 1) including, for example, disolvates (R.2(solvent)), trisolvates (R.3(solvent)), and the like, or hemisolvates, such as, for example, R.n/2(solvent), R.n/3(solvent), R.n/4(solvent) and the like, wherein n is an integer. Solvents herein include mixed solvents, for example, methanol/water, and as such, the solvates may incorporate one or more solvents within the solvate.

The term "acid hydrate" as used herein refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

G—X—Y=Z ⇌ X=Y—Z—G where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is H⁺, is also known as "prototropy." Tautomers are defined as isomers that arise from tautomerism, independent of whether the isomers are isolable.

ChemDraw version 8.0 or 10, (CambridgeSoft Corporation, Cambridge, Mass.) was used to name structures.

The following abbreviations are used in this disclosure and have the following definitions: ADP is adenosine diphosphate, ATP is adenosine triphosphate, dba is dibenzylideneacetone, DIEA is N,N-diisopropylethylamine, DMA is N,N-dimethylacetamide, DMF is N,N-dimethylformamide, DMSO is dimethylsulfoxide, DTT is dithiothreitol, EGTA is ethylene glycol tetraacetic acid, ESI is electrospray ionization, GST is glutathione S-transferase, "h" is hour or hours, HATU is 2-(7-Aza-1H-benzotriazole-1-yl)-1,1,3,3-tetramethyluronium hexafluorophosphate, HEPES is 4-(2-hydroxyethyl)-1-piperazineethanesulfonic acid, HPLC is high pressure (or performance) liquid chromatography, IC$_{50}$ is half maximal inhibitory concentration, MS is mass spectrometry, min is minutes, NADH is nicotinamide adenine dinucleotide, NMR is nuclear magnetic resonance, PBS is phosphate buffered saline, RT is room temperature, THF is tetrahydrofuran, Tris is tris(hydroxymethyl)aminomethane, and xantphos is 4,5-bis(diphenylphosphino)-9,9-dimethylxanthene.

Compounds

In one aspect, compounds of the Formula I are described:

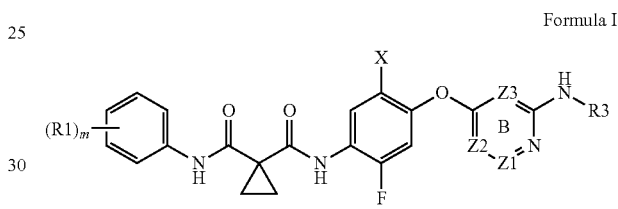

Formula I and pharmaceutically acceptable salts, hydrates, solvates, enantiomers, stereoisomers, and tautomers thereof;

wherein

X, B, Z1, Z2, Z3, R1, R2, R3, R4, R6, R7, R25, m, n and p are as defined above for Formula I; and each heterocyclyl and heteroaryl individually and independently has a C or N bonding hand.

In some embodiments, a ring N atom from the heterocyclyl is the bonding atom to —C(O) to form an amide, carbamate, or urea. In other embodiments, a ring N atom from the heteroaryl is the bonding atom to —C(O) to form an amide, carbamate, or urea.

In some embodiments, compounds of the Formula I are compounds of the Formula Ib:

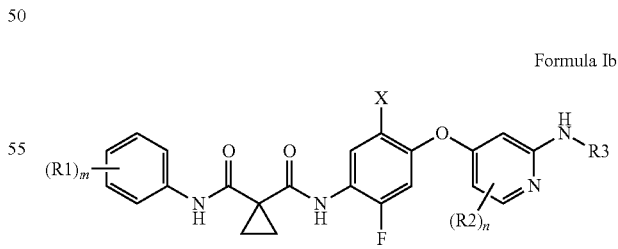

Formula Ib and pharmaceutically acceptable salts, hydrates, solvates, enantiomers, stereoisomers, and tautomers thereof;

wherein

X, R1, R2, R3, R4, R6, R7, R25, m, n and p are as defined above for Formula I; and n is 0, 1, or 2;

In some embodiments, compounds of the Formula I are compounds of the Formula Ic:

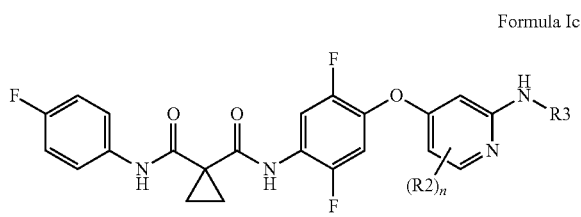

Formula Ic and pharmaceutically acceptable salts, hydrates, solvates, enantiomers, stereoisomers, and tautomers thereof;

wherein

R2, R3, R4, R6, R7, R25, m, n, and p are as defined above for Formula Ib.

In some embodiments, compounds of the Formula I are compounds of the Formula Ie:

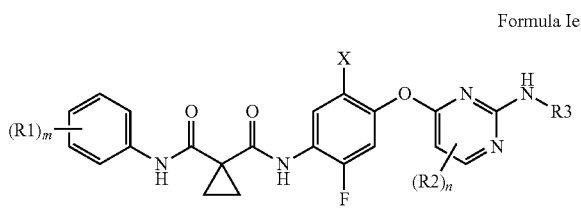

Formula Ie and pharmaceutically acceptable salts, hydrates, solvates, enantiomers, stereoisomers, and tautomers thereof;

wherein

X, R1, R2, R3, R4, R6, R7, R25, m, n, and p are as defined above for Formula Ib.

In some embodiments, compounds of the Formula I are compounds of the Formula If:

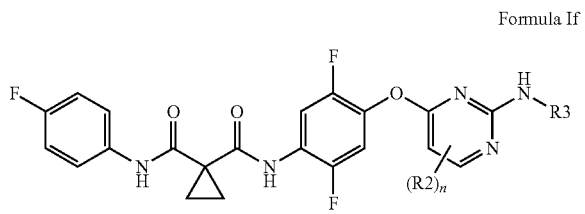

Formula If and pharmaceutically acceptable salts, hydrates, solvates, enantiomers, stereoisomers, and tautomers thereof;

wherein

R2, R3, R4, R6, R7, R25, m, n, and p are as defined above for Formula Ib.

In some embodiments, compounds of the Formula I are compounds of the Formula Ih:

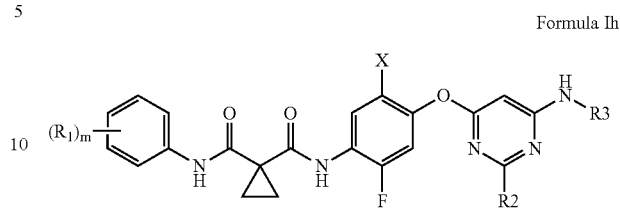

Formula Ih and pharmaceutically acceptable salts, hydrates, solvates, enantiomers, stereoisomers, and tautomers thereof;

wherein

X, R1, R2, R3, R4, R6, R7, R25, m, n and p are as defined above for Formula I.

In some embodiments, compounds of the Formula I are compounds of the Formula Ij:

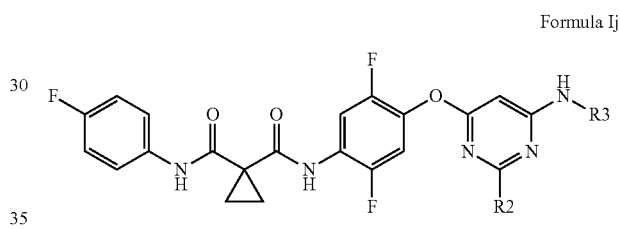

Formula Ij and pharmaceutically acceptable salts, hydrates, solvates, enantiomers, stereoisomers, and tautomers thereof;

wherein

R2, R3, R4, R6, R7, R25, m, n and p are as defined above for Formula I.

In some embodiments, compounds of the Formula I are compounds of the Formula Il:

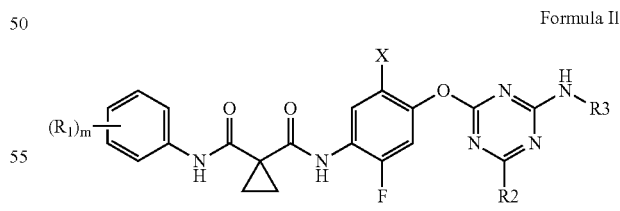

Formula Il and pharmaceutically acceptable salts, hydrates, solvates, enantiomers, stereoisomers, and tautomers thereof;

wherein

X, R1, R2, R3, R4, R6, R7, R25, m, n and p are as defined above for Formula I.

In some embodiments, compounds of the Formula I are compounds of the Formula Im:

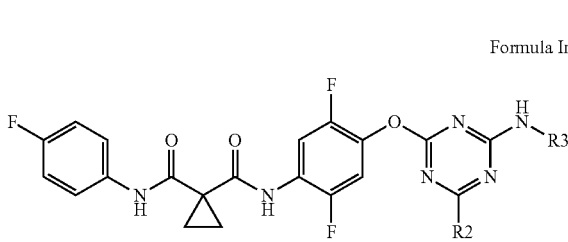

Formula Im and pharmaceutically acceptable salts, hydrates, solvates, enantiomers, stereoisomers, and tautomers thereof;

wherein

R2, R3, R4, R6, R7, R25, m, n and p are as defined above for Formula I.

The following embodiments are descriptive of Formula I, Formula Ib, Formula Ic, Formula Ih, and Formula Il.

In some embodiments, X is halogen. In other embodiments, X is F or Cl. In further embodiments, X is F.

In some embodiments, each R1 is individually and independently halogen. In other embodiments, each R1 is individually and independently F or Cl. In further embodiments, each R1 is F.

In some embodiments, m is 1 and R1 is halogen. In other embodiments, m is 1 and R1 is F or Cl. In further embodiments, m is 1 and R1 is F.

In some embodiments, X and each R1 is individually and independently halogen. In other embodiments, X and each R1 is individually and independently F or Cl. In further embodiments, X and each R1 is F.

In some embodiments, m is 1 and X and each R1 is individually and independently halogen. In other embodiments, m is 1 and X and each R1 is individually and independently F or Cl. In further embodiments m is 1 and X and each R1 is F.

The following embodiments are descriptive of Formula I, Formula Ib, Formula Ic, Formula Ie, Formula If, Formula Ih, Formula Ij, Formula Il, and Formula Im.

In some embodiments, R3 is —C(O)R4 and R4 is C1-C7 alkyl, C3-C8 cycloalkyl, —(CH$_2$)$_p$—CN, —(CH$_2$)$_p$—OR6, —(CH$_2$)$_p$—NR6(R7), or —(CH$_2$)$_p$—C4-C6-heterocyclyl, wherein each alkyl or alkylene is optionally substituted with one or two C1-C6 alkyl. In further embodiments, one alkyl or alkylene is substituted by one C1-C6 alkyl. In still further embodiments, one alkyl or alkylene is substituted by one C1-alkyl.

In some embodiments, R3 is —C(O)—C6-C10-aryl, —C(O)—C4-C6-heterocyclyl, or —C(O)—C5-C6-heteroaryl.

In illustrative embodiments, compounds disclosed herein are as set forth below.

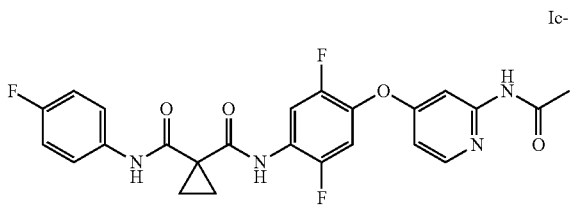

Ic-1

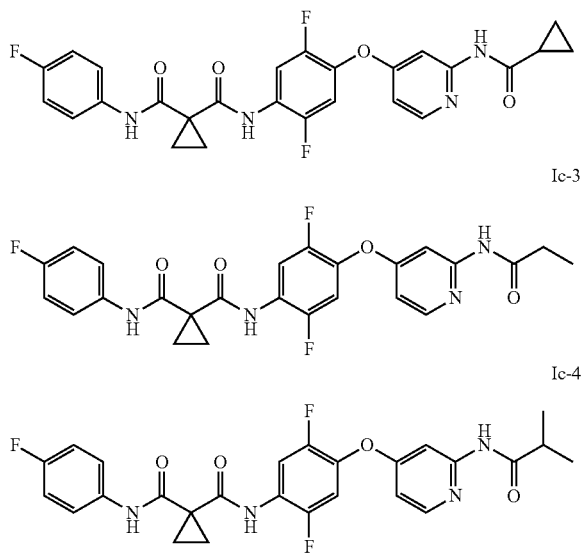

Ic-2

Ic-3

Ic-4

Utility

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms-, aberrant fusion protein forms, and mutant forms of c-MET kinase.

Administration of Compounds

In some embodiments, the compound is administered by a method selected from the group consisting of oral, parenteral, inhalation, and subcutaneous.

Treatment Methods

The disclosed methods also include treating individuals suffering from a condition selected from the group consisting of cancer, hyperproliferative diseases, metabolic diseases, neurodegenerative diseases or diseases characterized by angiogenesis. These methods comprise administering to such individuals compounds disclosed herein, and especially those of section 1, said diseases including, but not limited to, solid tumors, malignant melanomas, glioblastomas, ovarian cancer, pancreatic cancer, prostate cancer; lung cancers, breast cancers, kidney cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, gastrointestinal stromal tumors, colonic cancers, ocular diseases characterized by hyperproliferation leading to blindness including various retinopathies, diabetic retinopathy and age-related macular degeneration and hypereosinophilic syndrome, rheumatoid arthritis, asthma, chronic obstructive pulmonary disorder, mastocytosis, mast cell leukemia, a disease caused by c-MET kinase, oncogenic forms thereof, aberrant fusion proteins thereof and polymorphs thereof. The administration method is not critical, and may be from the group consisting of oral, parenteral, inhalation, and subcutaneous.

Pharmaceutical Preparations

The compounds disclosed herein may form a part of a pharmaceutical composition by combining one or more such compounds with a pharmaceutically acceptable carrier. Additionally, the compositions may include an additive selected from the group consisting of adjuvants, excipients, diluents, and stabilizers.

Methods of Making

The compounds of the invention are available by the general synthetic methods illustrated in the Schemes below and the accompanying examples.

Compounds 1 of the invention are assembled in a step-wise manner as illustrated in Scheme 1. Beginning with cyclopropane-1,1-dicarboxylic-acid 2, standard peptide coupling chemistry familiar to those skilled in the art is employed in the formation or a new amide bond with amine 3 to yield intermediate 4. Alternatively, it is recognized that in this case and in others to follow, a carboxylic acid moiety, such as found in 2, is masked as an ester or activated as an acid halide, anhydride, mixed anhydride, or as an activated ester. In the case of activated acid derivatives it should be understood that these compounds are optionally isolated as discrete intermediates prior to their union with amines 3 to form 4. Subsequent coupling of 4 with aniline 5, either by peptide coupling conditions or via an activated acid intermediate, yields compounds of the desired formula 1. Using similar strategies, carboxylic acid 2 is also, in some embodiments, first coupled with aniline 5 to yield intermediate 6, which is then in turn coupled with 3 to yield desired compound 1.

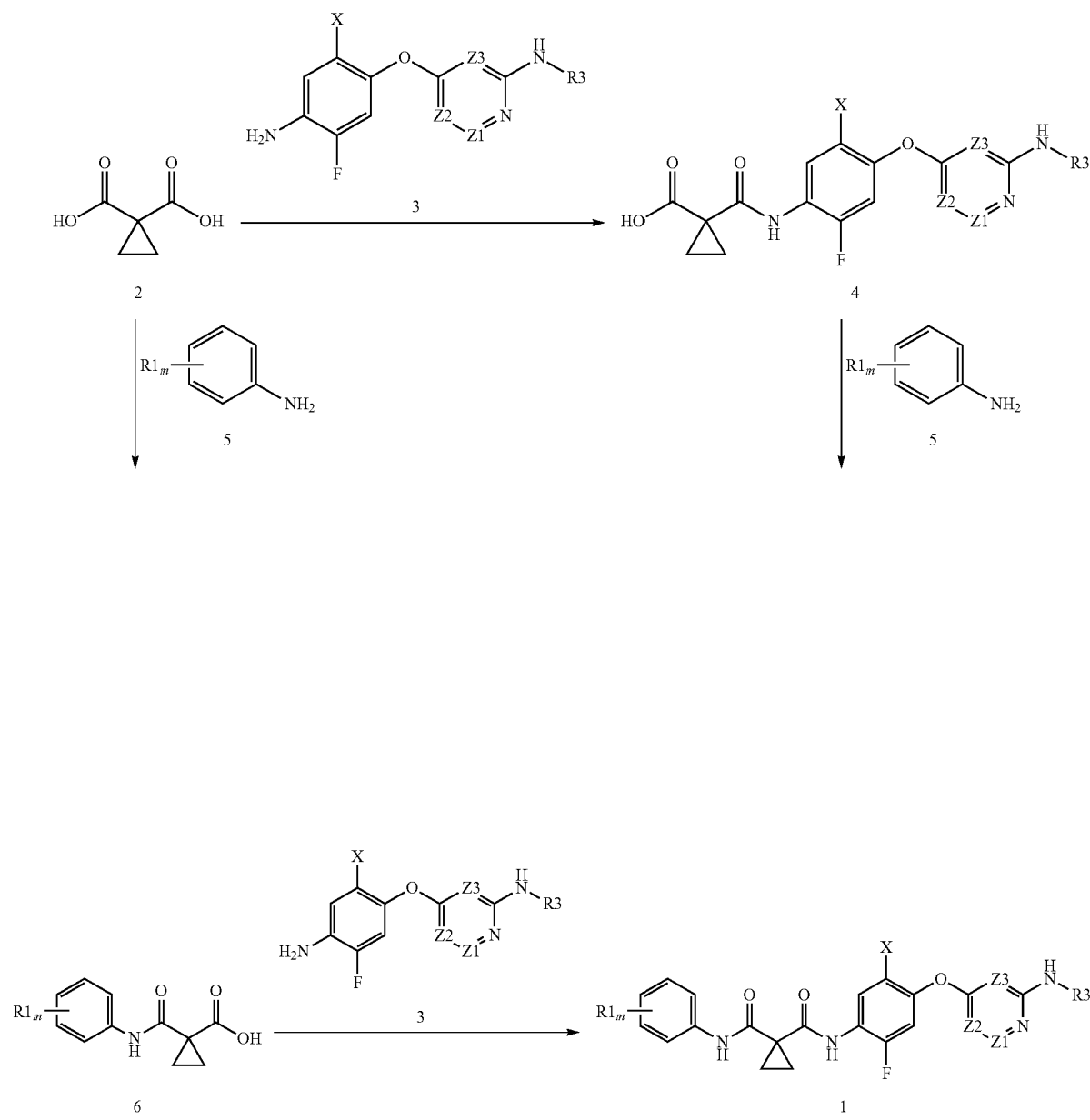

Scheme 1

Non-limiting examples of the strategies described in Scheme 1 are illustrated below. Scheme 2 illustrates the preparation of compound 10, an example of general formula 1 (wherein R1 is F, Z1, Z2, and Z3 are CH and R3 is —C(O)CH$_3$) by the general sequence of 2→4→1 (Scheme 1). Thus, as indicated below, the union of 1,1-cyclopropane bis-carboxylic acid 2 with amine 7 (an example of general amine 3) provides the amide/acid 8, an example of general intermediate 4. Conditions for the transformation include the in situ activation of bis-acid 2 by treatment with thionyl chloride in the presence of a tertiary base, such as triethylamine, followed by reaction with amine 7. Further reaction of 8 with amine 9 (an example of general intermediate 5) in the presence of a peptide coupling agent provides bis-amide 10. Coupling agents for the later transformation include TBTU (O-(benzotriazol-1-yl)-N,N,N',N'-tetramethyluronium tetrafluoroborate), PyBOP (benzotriazol-1-yloxy)tripyrrolidinophosphonium hexafluorophosphate), EDC (1-ethyl-3-(3-dimethylaminopropyl)carbodiimide hydrochloride) and BOP-Cl (bis(2-oxo-3-oxazolidinyl)phosphonic chloride).

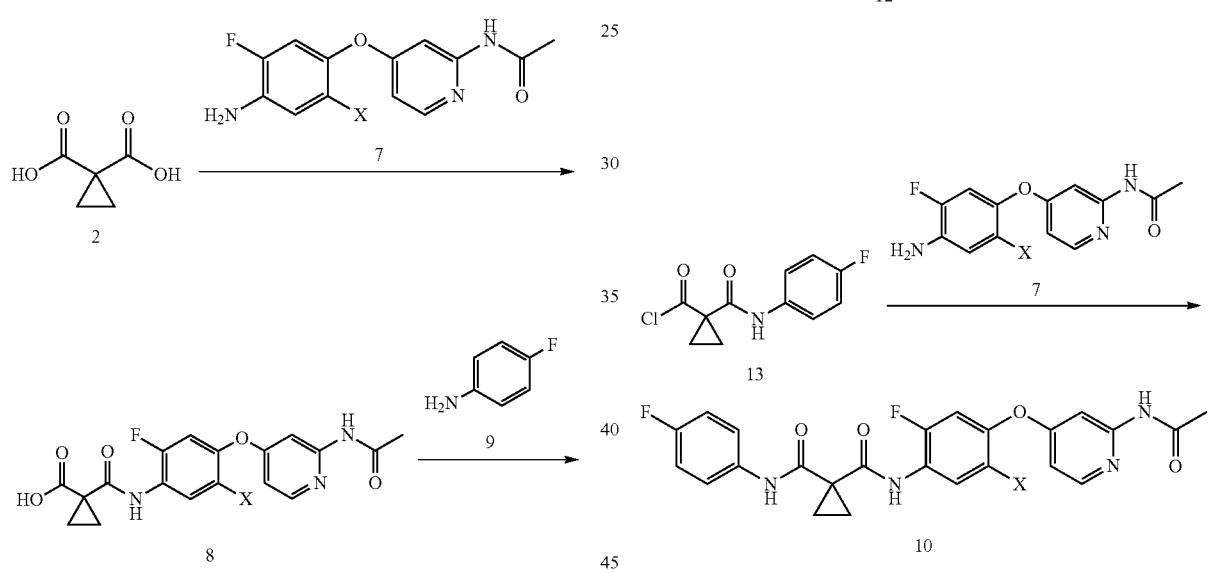

An example of an alternate route to 10, an example of general formula 1, is shown in Scheme 3. In this case the preparation begins with 11, in which one carboxylic acid moiety of dicarboxylic acid 2 is protected as a methyl ester. Using the conditions described above (Scheme 1) acid 11 and aniline 9 are coupled to yield methyl ester 12. Saponification of ester 12 using standard conditions (e.g., aqueous LiOH), followed by treatment with thionyl chloride, yields the activated acid chloride intermediate 13. Acid chloride 13 readily reacts with amine 7 in the presence of a base such as triethylamine or Hunig's base to yield example 10.

Amines of the general formula 3 that are useful for the invention are prepared by standard methods familiar to those skilled in the art. Several non-limiting examples are shown in the following schemes. A mixture of phenol 14 and benzamide 15, wherein LG is a leaving group such as a halide or sulfonate, are coupled in the presence of a base such as potassium tert-butoxide and a polar aprotic solvent at elevated temperatures (e.g., 100° C.) to yield 16 (Scheme 4). Protection of the aniline NH$_2$ of 16 with the appropriate protecting group (PG) familiar to one skilled in the art, such as a tert-butoxycarbonyl (BOC) group, followed by subjection to Hofmann rearrangement conditions results in the formation of 17. Acylation of 17 with R3-LG 18, followed by removal of the protecting group yields amine 3. In one instance, the reagent R3-LG (18) is a carboxylic acid (wherein LG is OH) that is coupled with the amino moiety of 17 using standard peptide Coupling agents, as described above. Alternately, reagent R3-LG (18) is an activated carboxylic acid derivative, such as an acid halide (wherein LG is halo) that undergoes reaction with amine 17 to provide 3.

Scheme 4

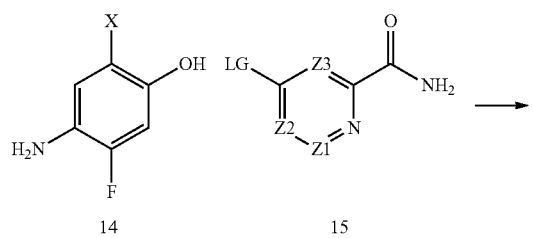

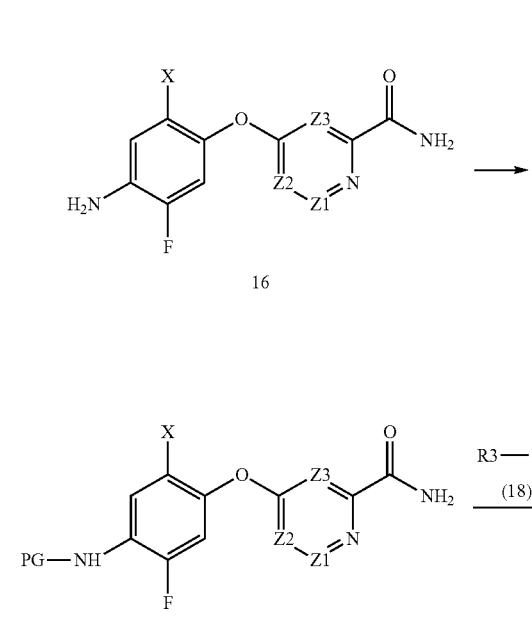

Scheme 5

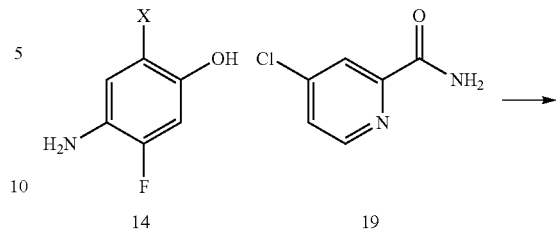

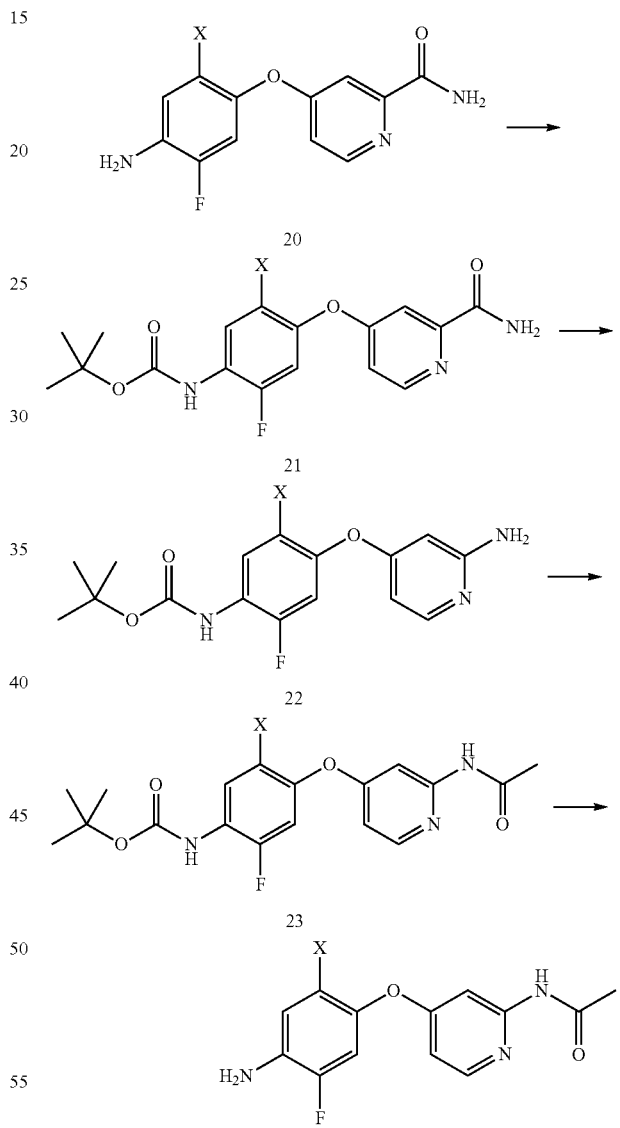

A non-limiting example of this synthetic route is shown in Scheme 5. Thus, the coupling of phenol 14 with 4-chloropicolinamide 19 (an example of intermediate 15, see Scheme 4) wherein Z1, Z2, and Z3 are CH, and LG is Cl) is effected by heating in the presence of a base to yield 20. Protection of the aniline moiety of 20 with a BOC group using conditions familiar to one skilled in the art affords 21. Amide 21 in turn undergoes a Hofmann rearrangement to yield aminopyridine 22. Conditions for the Hofmann rearrangement include bromine in aqueous KOH or addition of oxidants such as lead tetraacetate or hypervalent iodine reagents such as bis(trifluoroacetyl)iodobenzene in pyridine. Subsequent acylation of 22 with acetyl chloride (an example of R3-LG wherein LG is chloro) in a solution of pyridine yields 23. Removal of the BOC protecting group in a solution of HCl provides amine 7, an example of amine 3 wherein Z1, Z2, and Z3 are CH and R3 is —C(O)CH$_3$.

Alternately, a modified version of the route illustrated in Scheme 4 is shown in Scheme 6. The synthesis of 16, vide supra, is followed by its union with carboxylic acid 6 to yield 24 using either peptide coupling chemistry or an activated acid analog of 6. Subjecting 24 to Hofmann rearrangement conditions yields 25, which is then acylated with activated acid 18 to yield compounds of formula 1.

Scheme 6
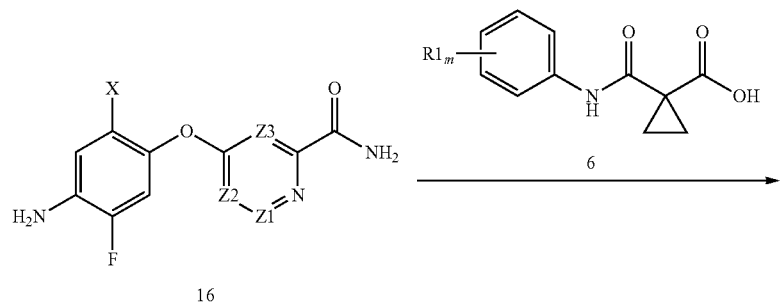
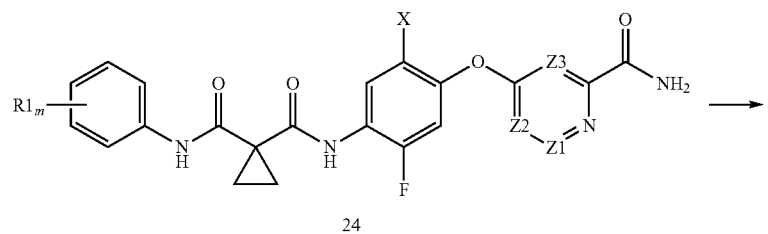
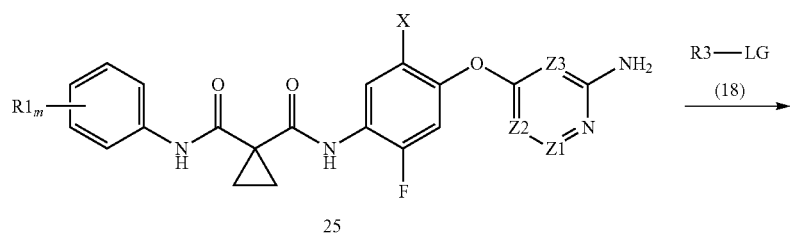
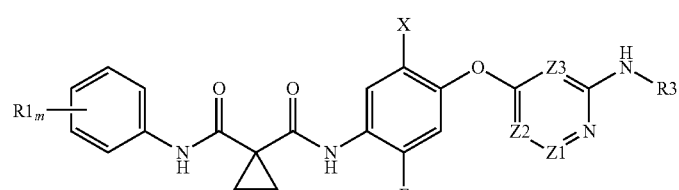

Amines of the general formula 3 are also accessed via 26 wherein Y is a typical leaving group in transition metal mediated coupling reactions (for example, chloride, bromide, or triflate) (Scheme 7). Treatment of 26 and amide 27 in an aprotic solvent, for example 1,4-dioxane, with a catalytic amount of Pd(OAc)$_2$ or Pd$_2$(dba)$_3$ and xantphos in the presence of cesium carbonate at elevated temperatures between 45° C. and 110° C. yields intermediate 3 (see Buchwald, et. al. *Org. Lett.* (2000), 2(8): 1101). Similarly, intermediate 28 is assembled from 26 and 6 using methods described in Scheme 3 and subsequently reacted with 27 using catalytic palladium and xantphos (vide supra) to yield compounds of formula 1.

Scheme 7

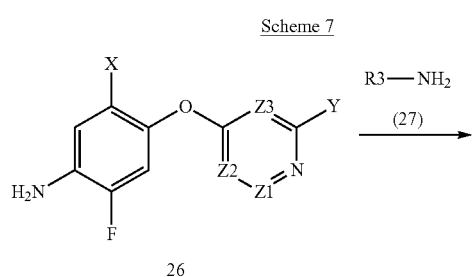

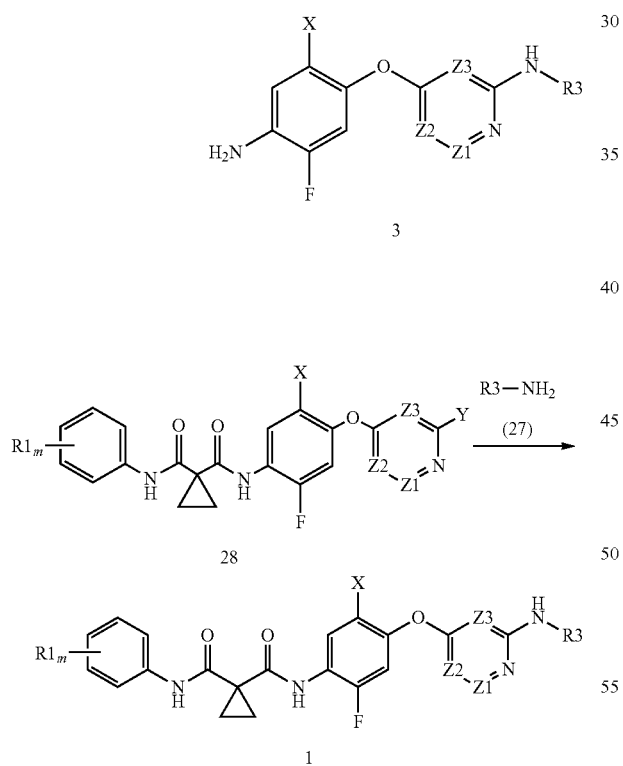

Amine 26 is synthesized in a variety of ways, including those shown below in the following non-limiting examples. As depicted, in Scheme 8, amino-phenol 14 and 29 (wherein LG is a leaving group in a nucleophilic substitution reaction, such as a halide or sulfonate) is coupled upon addition of a base such as potassium tert-butoxide in a solution of DMA at elevated temperatures of 80° C. to 100° C.

Scheme 8

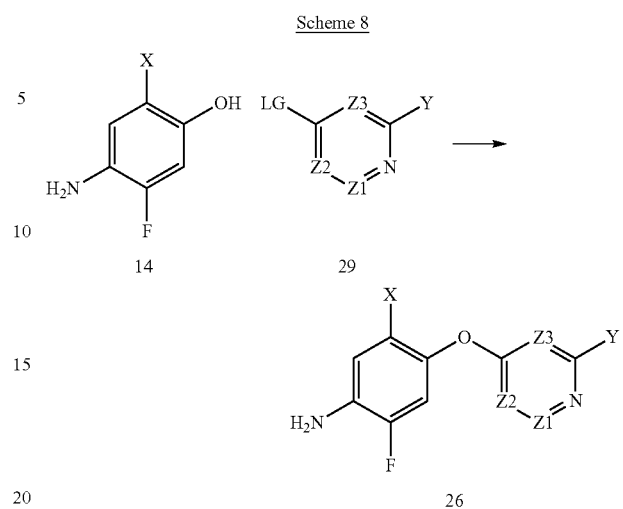

General amine 26 is also accessed via the 1-fluoro-4-nitrobenzene intermediate 30 (Scheme 9). The coupling of 30 with 31 proceeds at temperatures ranging from 0° C. to 80° C. in the presence of a base, for example sodium hydride. The resultant nitro intermediate 32 is then reduced using a variety of methods familiar to one skilled in the art to afford amine 26.

Scheme 9

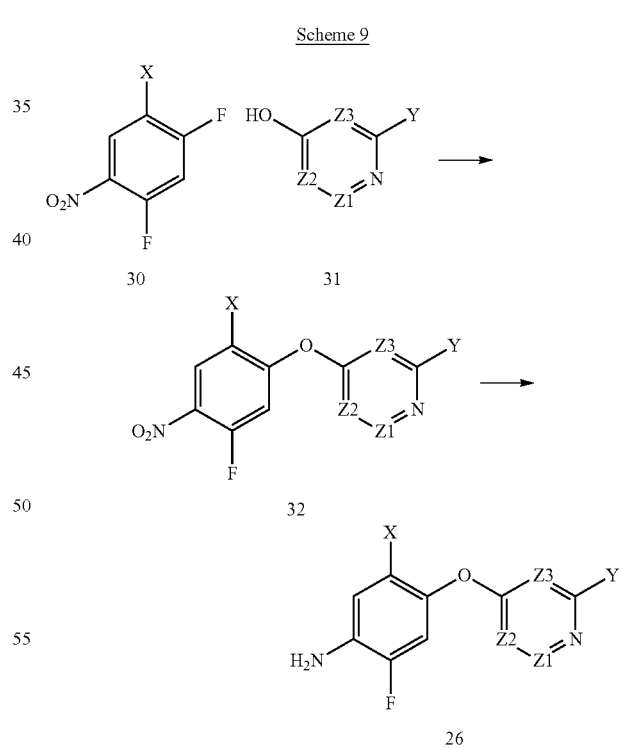

A non-limiting example of Scheme 9 is illustrated below for the synthesis of 36, a specific example of 26 wherein X is F, Y is Cl, and Z1, Z2, and Z3 are CH (Scheme 10). Addition of 1,2,4-trifluoro-5-nitrobenzene (33) to a solution of 2-chloropyridin-4-ol (34) and sodium hydride in DMF at 0° C. yields the nitro intermediate 35. The nitro moiety of 35 is subsequently reduced at RT in the presence of zinc dust and ammonium chloride in solution of methanol and THF to yield amine 36.

Scheme 10

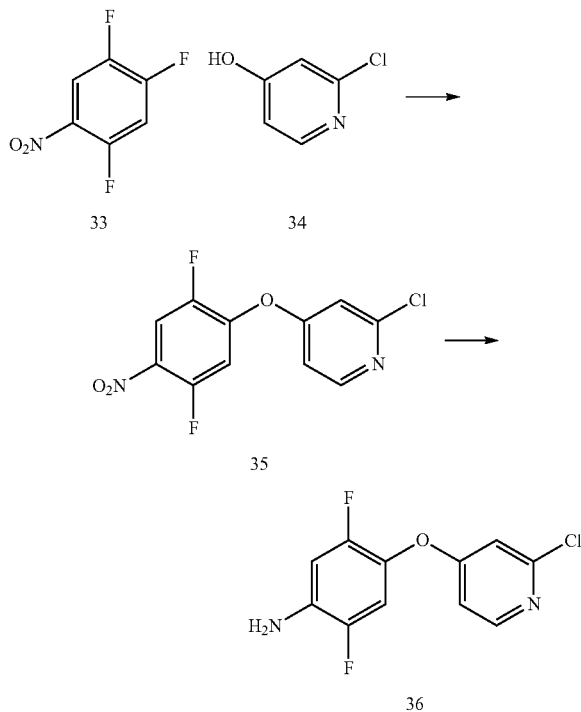

A non-limiting example of Scheme 7 is illustrated in Scheme 11, beginning with intermediate 36, prepared in Scheme 10. Thus, 36 readily reacts with acid chloride 13 (see Scheme 3) in the presence of triethylamine to yield chloro-pyridine 37. Chloro-pyridine 37 is then converted to 38, a specific example of 1 wherein R1 is F, X is F, Z1, Z2, and Z3 are CH and R3 is —C(O)CH$_3$, upon treatment with acetamide (an example of R3-NH$_2$ 27 where R3 is acetyl) and cesium carbonate in the presence of a catalytic amount of palladium acetate and xantphos.

Scheme 11

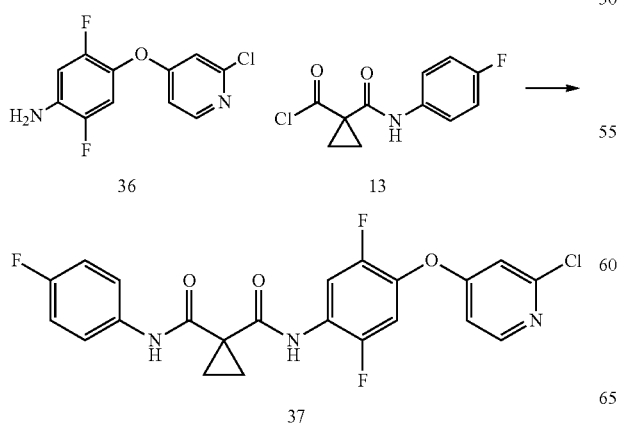

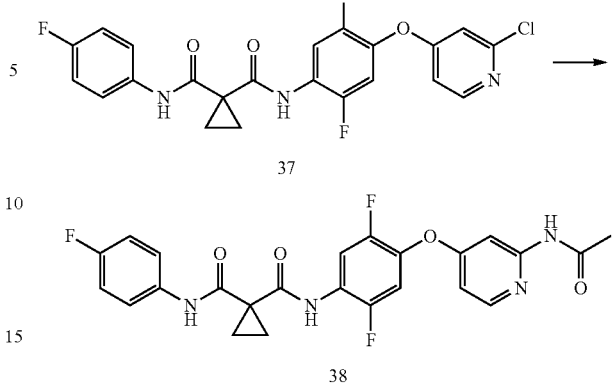

Using the synthetic procedures and methods described herein and methods known to those skilled in the art, the following compounds were made:

N-(4-(2-acetamidopyridin-4-yloxy)-2,5-difluorophenyl)-N'-(4-fluorophenyl)cyclopropane-1,1-dicarboxamide, N-(4-(2-acetamidopyridin-4-yloxy)-5-chloro-2-fluorophenyl)-N'-(4-fluorophenyl)cyclopropane-1,1-dicarboxamide, N-(4-(2-acetamidopyridin-4-yloxy)-2,5-difluorophenyl)-N'-phenylcyclopropane-1,1-dicarboxamide, N-(4-(2-(2-(dimethylamino)acetamido)pyridin-4-yloxy)-2,5-difluorophenyl)-N'-(4-fluorophenyl)cyclopropane-1,1-dicarboxamide, N-(4-(2-acetamidopyrimidin-4-yloxy)-2,5-difluorophenyl)-N'-(4-fluorophenyl)cyclopropane-1,1-dicarboxamide, N-(4-(2-(cyclopropanecarboxamido)pyridin-4-yloxy)-2,5-difluorophenyl)-N'-(4-fluorophenyl)cyclopropane-1,1-dicarboxamide, N-(2,5-difluoro-4-(2-propionamidopyridin-4-yloxy)phenyl)-N'-(4-fluorophenyl)cyclopropane-1,1-dicarboxamide, N-(2,5-difluoro-4-((2-(2-methoxyacetamido)pyridin-4-yl)oxy)phenyl)-N'-(4-fluorophenyl)cyclopropane-1,1-dicarboxamide, N-(2,5-difluoro-4-(2-isobutyramidopyridin-4-yloxy)phenyl)-N'-(4-fluorophenyl)cyclopropane-1,1-dicarboxamide, N-(4-(2-(2-cyanoacetamido)pyridin-4-yloxy)-2,5-difluorophenyl)-N'-(4-fluorophenyl)cyclopropane-1,1-dicarboxamide, N-(4-(2-(azetidine-3-carboxamido)pyridin-4-yloxy)-2,5-difluorophenyl)-N'-(4-fluorophenyl)cyclopropane-1,1-dicarboxamide, N-(4-(2-(cyclobutanecarboxamido)pyridin-4-yloxy)-2,5-difluorophenyl)-N'-(4-fluorophenyl)cyclopropane-1,1-dicarboxamide, (R)—N-(2,5-difluoro-4-((2-(2-methoxypropanamido)pyridin-4-yl)oxy)phenyl)-N'-(4-fluorophenyl)cyclopropane-1,1-dicarboxamide, R)—N-(2,5-difluoro-4-((2-(2-hydroxypropanamido)pyridin-4-yl)oxy)phenyl)-N'-(4-fluorophenyl)cyclopropane-1,1-dicarboxamide, N-(2,5-difluoro-4-((2-pivalamidopyridin-4-yl)oxy)phenyl)-N'-(4-fluorophenyl)cyclopropane-1,1-dicarboxamide, (S)—N-(2,5-difluoro-4-((2-(2-methoxypropanamido)pyridin-4-yl)oxy)phenyl)-N-(4-fluorophenyl)cyclopropane-1,1-dicarboxamide, (S)—1-((4-(2,5-difluoro-4-(1-((4-fluorophenyl)carbamoyl)cyclopropanecarboxamido)phenoxy)pyridin-2-yl)amino)-1-oxopropan-2-yl acetate, and N-(2,5-difluoro-4-((2-(2-fluoro-2-methylpropanamido)pyridin-4-yl)oxy)phenyl)-N'-(4-fluorophenyl)cyclopropane-1,1-dicarboxamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example A1

Sodium hydride (60% by weight in mineral oil) (3.08 g, 77 mmol) was placed in a 500 mL round bottom flask flushed with argon. DMF (140 mL) was added and the mixture was cooled in an ice bath. 2-Chloro-4-hydroxypyridine (7.68 g, 59.3 mmol) was then added slowly over 45 minutes. After addition of the hydroxypyridine was complete 2,4,5-trifluoronitrobenzene (10.5 g, 59.3 mmol) was added as a solution in DMF (29 mL). The mixture was warmed to room temperature and stirred for 18 hours. The reaction mixture was concentrated under reduced pressure to remove the majority of DMF in the mixture, and was then partitioned between ethyl acetate (300 mL) and 10% aqueous lithium chloride (150 mL). A precipitate formed which was removed via suction filtration and then the layers were separated. The organic layer was washed with additional 10% aqueous lithium chloride (2×150 mL), saturated aqueous sodium bicarbonate (150 mL) and brine (150 mL). The organic layer was dried over magnesium sulfate and evaporated to yield a dark red solid which was purified by silica gel chromatography (10 to 30% ethyl acetate/hexane) to give 2-chloro-4-(2,5-difluoro-4-nitrophenoxy)pyridine (13.56 g, 80% yield) as a yellow solid. $^1$H NMR (400 MHz, DMSO-$d_6$): δ 8.45 (dd, 1H), 8.39 (d, 1H), 7.87 (dd, 1H), 7.39 (d, 1H), 7.24 (dd, 1H); MS (ESI) m/z: 287.0 (M+H$^+$).

2-Chloro-4-(2,5-difluoro-4-nitrophenoxy)pyridine (13.06 g, 45.6 mmol) was dissolved in methanol (228 mL) and THF (228 mL) and cooled in an ice bath. Ammonium chloride (24.37 g, 456 mmol) was added, followed by zinc dust (29.8 g, 456 mmol), and the mixture was stirred in an ice bath for 30 minutes. After 30 minutes the ice bath was removed and the reaction mixture was allowed to warm to room temperature. After an additional hour of stirring the mixture was filtered through Celite®, which was washed well with methanol. The filtrate was concentrated under reduced pressure and the residue was partitioned between ethyl acetate (200 mL) and water (100 mL). The organic layer was washed with additional water (50 mL) and brine (100 mL), dried over magnesium sulfate, and concentrated to give 4-(2-chloropyridin-4-yloxy)-2,5-difluorobenzenamine (11.60 g, 99% yield) as a light brown solid. MS (ESI) m/z: 257.0 (M+H$^+$).

Example A2

2-Chloro-4-hydroxypyridine (0.319 g, 2.460 mmol) was dissolved in DMF (10 mL) under argon and cooled to −15° C. Sodium hydride (60% in mineral oil) (0.148 g, 3.69 mmol) was added slowly and the mixture was stirred for 15 minutes. 5-Chloro-2,4-difluoronitrobenzene (0.5 g, 2.58 mmol) was then added all at once as a solution in DMF (2 mL). The reaction mixture stirred at −15° C. for 1 hour and then additional 5-chloro-2,4-difluoronitrobenzene (0.075 g) was added. The mixture stirred at −15° C. for an additional 15 hours and was then warmed to room temperature and diluted with ethyl acetate (100 mL) and washed with 10% aqueous lithium chloride (3×75 mL) and brine (75 mL). The organic layer was dried over magnesium sulfate and evaporated to yield an orange oil, which was then purified by silica gel chromatography (0 to 30% ethyl acetate/hexane) to give 2-chloro-4-(2-chloro-5-fluoro-4-nitrophenoxy)pyridine (0.64 g, 86% yield) as a light yellow oil. $^1$H NMR (400 MHz, DMSO-$d_6$): δ 8.57 (dd, 1H), 8.36 (dd, 1H), 7.87 (dd, 1H), 7.32 (dd, 1H), 7.19 (m, 1H); MS (ESI) m/z: 303.0 (M+H$^+$).

2-Chloro-4-(2-chloro-5-fluoro-4-nitrophenoxy)pyridine (0.64 g, 2.112 mmol) was dissolved in methanol (50 mL) and THF (50.0 mL). Ammonium chloride (1.130 g, 21.12 mmol) was added, followed by zinc dust (1.381 g, 21.12 mmol). The suspension stirred at room temperature for 3 hours and was then filtered through Celite® and evaporated to yield a brown solid, which was then partitioned between a 4:1 mixture of ethyl acetate and THF (150 mL) and water (75 mL). The organic layer was washed with brine, dried over magnesium sulfate, and evaporated to afford 5-chloro-4-(2-chloropyridin-4-yloxy)-2-fluorobenzenamine (0.505 g, 88% yield) as a thick brown oil. MS (ESI) m/z: 273.0 (M+H$^+$).

Example A3

A solution of 4,6-dichloro-pyrimidin-2-ylamine (5 g, 30 mmol) and acetyl chloride (4.7 g, 60 mmol) in acetic acid (200 mL) was stirred at 80° C. under nitrogen overnight. The solution was cooled to RT and water (150 mL) was added. The mixture was extracted with ethyl acetate (3×150 mL), and the combined organics were washed with brine, dried over sodium sulfate and concentrated to give N-(4,6-dichloro-pyrimidin-2-yl)-acetamide (5.0 g, 79% yield).

A solution of 4-amino-2,5-difluoro-phenol (3.5 g, 24 mmol), N-(4,6-dichloro-pyrimidin-2-yl)-acetamide (5.30 g, 24 mmol) and potassium carbonate (3.4 g, 24 mmol) in DMF (100 mL) was stirred at 50° C. under nitrogen overnight. After cooling to room temperature the reaction mixture was suspended in water (300 mL) and extracted with ethyl acetate (3×200 mL). The combined organic layers was washed with brine, dried over sodium sulfate and concentrated. The crude product was purified by silica gel chromatography (15%-20% ethyl acetate in petroleum ether) to give N-[4-(4-amino-2,5-difluoro-phenoxy)-6-chloro-pyrimidin-2-yl]-acetamide (3.3 g, 44% yield) as a white solid. $^1$HNMR (400 MHz, DMSO-$d_6$): δ 10.72 (s, 1H), 7.20-7.24 (dd, J=11.2 Hz, J=7.6 Hz, 1H), 7.00 (s, 1H), 6.64 (dd, J=12.0 Hz, J=8.4 Hz, 1H), 5.48 (s, 2H), 2.03 (s, 3H).

A mixture of N-[4-(4-amino-2,5-difluoro-phenoxy)-6-chloro-pyrimidin-2-yl]-acetamide (3.3 g, 10.5 mmol) and palladium on carbon (1.0 g, 10%) in methanol (100 mL) was stirred under H$_2$ (1 atm) at 15° C. for 4 h. The reaction mixture was filtered and the filtrate was concentrated under reduced pressure to give N-[4-(4-amino-2,5-difluoro-phenoxy)-pyrimidin-2-yl]-acetamide (2.4 g, 82% yield) as a pale yellow solid. $^1$HNMR (400 MHz, DMSO-$d_6$): δ10.37 (s, 1H), 8.44 (d, J=5.7 Hz, 1H), 7.15 (dd, J=11.4 Hz, J=4.8 Hz, 1H) 6.71 (d, J=5.7 Hz, 1H), 6.65 (dd. J=12.3 Hz, J=8.4 Hz, 1H), 5.40 (s, 2H), 1.99 (s, 3H); MS (ESI) m/z: 281.2[M+H]$^+$.

Example B1

Cyclopropane-1,1-dicarboxylic acid monomethylester (2 g, 13.88 mmol) was dissolved in DMF (28 mL) and 4-fluoroaniline (1.999 mL, 20.82 mmol) was added, followed by diisopropylethylamine (12.12 mL, 69.4 mmol) and O-(benzotriazol-1-yl)-N,N,N',N'-tetramethyluronium tetrafluoroborate (8.91 g, 27.8 mmol). The mixture stirred at room temperature for 15 hours and was then diluted with ethyl acetate (200 mL) and washed with 10% aqueous lithium chloride (3×100 mL) and brine (100 mL). The organic layer was dried over magnesium sulfate and evaporated to yield the crude product as a brown solid. It was purified by silica gel chromatography (0 to 20% ethyl acetate/hexane) to give methyl 1-((4-fluorophenyl)carbamoyl)cyclopropanecarboxylate (3.28 g, 99% yield) as a light yellow solid. $^1$H NMR (400 MHz, DMSO-d$_6$): δ 10.32 (s, 1H), 7.60 (m, 2H), 7.12 (m, 2H)), 3.66 (s, 3H), 1.38 (m, 4H); MS (ESI) m/z: 238.1 (M+H$^+$).

Methyl 1-((4-fluorophenyl)carbamoyl)cyclopropanecarboxylate (3.28 g, 14.00 mmol) was dissolved in THF (23.34 mL), water (11.67 mL) was added, followed by lithium hydroxide monohydrate (1.763 g, 42.0 mmol), and the mixture stirred at room temperature for 30 minutes. After this time the THF was removed under reduced pressure and the pH of the water layer was adjusted to ~5 with 2 M HCl while the solution was cooled in an ice bath. The precipitate that formed was dissolved in ethyl acetate (125 mL) and the layers were separated. The organic layer was washed with water (100 mL) and brine (100 mL) and then dried over magnesium sulfate. Evaporation of the solvent yielded 1-((4-fluorophenyl)carbamoyl)cyclopropanecarboxylic acid (2.952 g, 94% yield) as an off white powder. $^1$H NMR (400 MHz, DMSO-d$_6$): δ 13.06 (broad s, 1H), 10.56 (s, 1H), 7.60 (m, 2H), 7.12 (m, 2H), 1.39 (s, 4H); MS (ESI) m/z: 224.1 (M+H$^+$).

1-((4-Fluorophenyl)carbamoyl)cyclopropanecarboxylic acid (1.484 g, 6.65 mmol) was dissolved in thionyl chloride (14 mL, 192 mmol) at 60° C. The reaction mixture stirred for 30 minutes under argon, and then the solution was cooled to room temperature and toluene (10 mL) was added. The mixture was concentrated under reduced pressure. Additional toluene (10 mL) was added, and then the mixture was again concentrated. This was repeated twice more. The off-white solid that was obtained, 1-((4-fluorophenyl)carbamoyl)cyclopropanecarbonyl chloride, was used immediately in the next step without purification, assuming a 100% yield. MS (ESI) m/z (methanol quench): 238.1 (M+H$^+$).

Example B2

Cyclopropane-1,1-dicarboxylic acid monomethyl ester (0.4 g, 2.78 mmol) was, dissolved in DMF (5.55 mL) and aniline (0.380 mL, 4.16 mmol) was added, followed by diisopropylethylamine (2.424 mL, 13.88 mmol) and O-(benzotriazol-1-yl)-N,N,N',N'-tetramethyluronium tetrafluoroborate (1.782 g, 5.55 mmol). The reaction mixture was stirred at room temperature for 18 hours and was then diluted with ethyl acetate (70 mL) and washed with 10% aqueous lithium chloride (3×40 mL), saturated aqueous ammonium chloride (40 mL), saturated aqueous sodium bicarbonate (40 mL) and brine (40 mL). The organic layer was dried over magnesium sulfate and evaporated to yield a dark brown oil. It was purified by silica gel chromatography (0 to 20% ethyl acetate/hexane) to yield methyl 1-(phenylcarbamoyl)cyclopropanecarboxylate (0.607 g, 100% yield) as a light peach solid. $^1$H NMR (400 MHz, DMSO-d$_6$): δ 10.29 (s, 1H), 7.58 (d, 2H), 7.28 (t, 2H), 7.04 (t, 1H), 3.66 (s, 3H), 1.37 (m, 4H); MS (ESI) m/z: 220.1 (M+H$^+$).

Methyl 1-(phenylcarbamoyl)cyclopropanecarboxylate (0.607 g, 2.77 mmol) was dissolved in a mixture of THF (3.5 mL) and water (3.50 mL), lithium hydroxide monohydrate (0.349 g, 8.31 mmol) was added, and the mixture was stirred at room temperature for 1 hour. The THF was removed under reduced pressure and additional water (20 mL) was added. The solution was acidified to ~pH 4 with 2 M HCl and the off white solid that precipitated was collected by suction filtration and washed with additional water to give 1-(phenylcarbamoyl)cyclopropanecarboxylic acid (0.482 g, 85% yield). MS (ESI) m/z: 206.0 (M+H$^+$)

1-(Phenylcarbamoyl)cyclopropanecarboxylic acid (0.115 g, 0.559 mmol) was dissolved in thionyl chloride (1.224 mL, 16.77 mmol) and heated to 60° C. under argon. After 1 hour the reaction mixture was cooled to room temperature and evaporated to dryness under reduced pressure. Toluene (2 mL) was added and evaporated three times and the pale peach oil that remained, 1-(phenylcarbamoyl)cyclopropanecarbonyl chloride, was used immediately in the next step assuming a 100% yield. MS (ESI) m/z (methanol quench): 220.1 (M+H$^+$).

Example 1

Compound D

Example A1 (2.136 g, 8.32 mmol) was dissolved in dry THF (63 mL) and triethylamine (1.508 mL, 10.82 mmol) was added. To this solution was added Example B1 (2.414 g, 9.99 mmol) in dry THF (20 mL). The mixture stirred at room temperature for 30 minutes. The triethylamine hydrochloride was removed from the reaction mixture by suction filtration. The filtrate was evaporated to yield an orange oil which was purified by silica gel chromatography (10% to 50% ethyl acetate/hexane) to yield N-(4-(2-chloropyridin-4-yloxy)-2,5-difluorophenyl)-N'-(4-fluorophenyl)cyclopropane-1,1-dicarboxamide (3.819 g, 99% yield) as a cream-colored solid. $^1$H NMR (400 MHz, DMSO-d$_6$): δ11.13 (s, 1H), 9.73 (s, 1H), 8.30 (d, 1H), 8.13 (dd, 1H), 7.57 (m, 3H), 7.16 (m, 3H), 7.02 (dd, 1H), 1.64 (m, 2H), 1.57 (m, 2H); MS (ESI) m/z: 462.1 (M+H$^+$).

N-(4-(2-chloropyridin-4-yloxy)-2,5-difluorophenyl)-N'-(4-fluorophenyl)cyclopropane-1,1-dicarboxamide (3.819 g, 8.27 mmol), acetamide (2.442 g, 41.3 mmol), cesium carbonate (4.04 g, 12.40 mmol), and xantphos (0.469 g, 0.810 mmol) were stirred in dry dioxane (59.1 mL) while argon was bubbled through the mixture for 15 minutes. After this time palladium acetate (0.139 g, 0.620 mmol) was added, and argon was bubbled through the solution for an additional 10 minutes. The round bottom flask was then fitted with a reflux condenser, flushed with argon, and heated to 100° C. gradually from room temperature while under a balloon of argon. After 3.5 hours at 100° C. the reaction mixture was cooled to room temperature. The reaction mixture was diluted with a 4:1 mixture of ethyl acetate and THF (300 mL) and water (100 mL). A bright yellow solid was removed by suction filtration and discarded. The organic layer was separated from the aqueous and washed with brine (200 mL). In addition, the aqueous layer was back-extracted with the ethyl acetate/THF mixture (100 mL), which was then also washed with brine (50 mL). The combined organic layers were dried over magnesium sulfate and evaporated to yield a peach-colored oil. It was stirred in dichloromethane (50 mL) for 1.5 hours, and a white solid formed which was collected by suction filtration and washed with more dichloromethane to give N-(4-(2-acetamidopyridin-4-yloxy)-2,5-difluorophenyl)-N'-(4-fluorophenyl)cyclopropane-1,1-dicarboxamide (3.328 g, 83% yield). $^1$H NMR (400 MHz, DMSO-d$_6$): δ 11.00 (s, 1H), 10.59 (s, 1H), 9.79 (s, 1H), 8.19 (d, 1H), 8.07 (dd, 1H), 7.65

(d, 1H), 7.57 (m, 3H), 7.16 (m, 2H), 6.71 (dd, 1H), 2.02 (s, 3H), 1.62 (m, 2H), 1.57 (m, 2H); MS (ESI) m/z: 485.1 (M+H$^+$).

Example 2

A solution of Example A2 (0.147 g, 0.538 mmol) in dry THF (5.38 mL) with triethylamine (0.098 mL, 0.700 mmol) was added to Example B1 (0.169 g, 0.699 mmol). The mixture was stirred under argon for 20 minutes at room temperature. The reaction mixture was then filtered through a frit in order to remove the solid triethylamine hydrochloride that had precipitated. The filtrate was concentrated under reduced pressure to yield a pale orange oil which was purified by silica gel chromatography (0 to 50% ethyl acetate/hexane) to yield N-(5-chloro-4-(2-chloropyridin-4-yloxy)-2-fluorophenyl)-N'-(4-fluorophenyl)cyclopropane-1,1-dicarboxamide (0.203 g, 79% yield) as a clear sticky oil. $^1$H NMR (400 MHz, DMSO-d$_6$): δ 11.04 (s, 1H), 9.77 (s, 1H), 8.30 (m, 2H), 7.58 (m, 3H), 7.16 (t, 2H), 7.07 (d, 1H), 6.96 (dd, 1H), 1.63 (m, 2H), 1.56 (m, 2H); MS (ESI) m/z: 478.1 (M+H$^+$).

N-(5-cloro-4-(2-chloropyridin-4-yloxy)-2-fluorophenyl)-N'-(4-fluorophenyl)cyclopropane-1,1-dicarboxamide (0.200 g, 0.418 mmol), acetamide (0.124 g, 2.091 mmol), cesium carbonate (0.136 g, 0.418 mmol), and xantphos (0.017 g, 0.029 mmol) were dissolved in dry dioxane (3 mL) in a 25 mL round bottom flask. Argon was bubbled through the reaction mixture for 5 minutes, and then palladium acetate (4.69 mg, 0.021 mmol) was added. The mixture was again degassed for five minutes, and then the reaction flask was fitted with a reflux condenser. The system was flushed with argon and then heated at 100° C. under a balloon of argon for 3 hours. The reaction mixture was cooled to room temperature and diluted with water (30 mL) and a 4:1 mixture of ethyl acetate and THF (150 mL). The layers were separated, and the aqueous layer was washed with additional ethyl acetate/THF solution. The organic layers were combined and concentrated to yield a sticky orange oil. Upon addition of methanol (3 mL) a fine cream-colored precipitate formed, which was collected by suction filtration and washed with a small portion of dichloromethane to yield N-(4-(2-acetamidopyridin-4-yloxy)-5-chloro-2-fluorophenyl)-N'-(4-fluorophenyl)cyclopropane-1,1-dicarboxamide (0.100 g, 47.7% yield). $^1$H NMR (400 MHz, DMSO-d$_6$): δ 10.91 (s, 1H), 10.58 (s, 1H), 9.83 (s, 1H), 8.23 (d, 1H), 8.18 (d, 1H), 7.58 (m, 4H), 7.15 (m, 2H), 6.65 (dd, 1H), 2.02 (s, 3H), 1.61 (m, 2H), 1.56 (m, 2H); MS (ESI) m/z: 501.1 (M+H$^+$).

Example 3

Example A1 (0.12 g, 0.468 mmol) was dissolved in dry THF (4.68 mL) and triethylamine (0.085 mL, 0.608 mmol) was added. This solution was added to Example B2 (0.125 g, 0.561 mmol) and the mixture stirred under argon at room temperature for 2 hours. The reaction mixture was filtered to remove triethylamine hydrochloride salt and the filtrate was evaporated to yield a light peach oil which was purified by silica gel chromatography (10 to 50% ethyl acetate/hexane) to yield N-(4-(2-chloropyridin-4-yloxy)-2,5-difluorophenyl)-N'-phenylcyclopropane-1,1-dicarboxamide (0.164 g, 79% yield) as a clear solid. $^1$H NMR (400 MHz, DMSO-d$_6$): δ 11.10 (s, 1H), 9.71 (s, 1H), 8.31 (d, 1H), 8.12 (dd, 1H), 7.60 (dd, 1H), 7.55 (m, 2H), 7.32 (t, 2H), 7.14 (d, 1H), 7.10 (m, 1H), 7.02 (dd, 1H), 1.65 (m, 2H), 1.58 (m, 2H); MS (ESI) m/z: 444.1 (M+H$^+$).

N-(4-(2-chloropyridin-4-yloxy)-2,5-difluorophenyl)-N'-phenylcyclopropane-1,1-dicarboxamide (0.162 g, 0.365 mmol), acetamide (0.108 g, 1.825 mmol), cesium carbonate (0.178 g, 0.548 mmol), and xantphos (0.021 g, 0.036 mmol) were combined in dry dioxane (2.61 mL) and argon was bubbled through the mixture for 5 minutes. Palladium acetate (6.15 mg, 0.027 mmol) was added, and argon was bubbled through the mixture for an additional 5 minutes. The reaction flask was fitted with a reflux condenser and a balloon of argon and the mixture was heated at 100° C. for 20 hours. The reaction mixture was cooled to room temperature and partitioned between a 4:1 mixture of ethyl acetate and THF (50 mL) and water (50 mL). The aqueous layer was removed and the organic layer was washed with additional water (50 mL) and brine (50 mL). The organic layer was dried over magnesium sulfate and evaporated under reduced pressure to yield a light peach-colored film. Dichloromethane (10 mL) was added and after a few minutes solid began to precipitate. Sonication was used to precipitate out more solid. After sitting for 30 minutes the bright white solid was collected by suction filtration and washed with additional dichloromethane to give N-(4-(2-acetamidopyridin-4-yloxy)-2,5-difluorophenyl)-N'-phenylcyclopropane-1,1-dicarboxamide (0.099 g, 58% yield). $^1$H NMR (400 MHz, DMSO-d$_6$): δ 10.98 (s, 1H), 10.59 (s, 1H), 9.78 (s, 1H), 8.19 (d, 1H), 8.07 (dd, 1H), 7.65 (d, 1H), 7.55 (m, 3H), 7.32 (m, 2H), 7.09 (t, 1H), 6.71 (dd, 1H), 2.02 (s, 3H), 1.63 (m, 2H), 1.57 (m, 2H); MS (ESI) m/z: 467.2 (M+H$^+$).

Example 4

2-Bromoacetamide (1 g, 7.25 mmol) was dissolved in acetonitrile (10.35 mL) and 2 M dimethylamine in THF (12 mL, 24.00 mmol) was added. The mixture stirred under argon at room temperature for 48 hours. The reaction mixture was evaporated under reduced pressure and the residue was re-dissolved in a 1:1 mixture of dichloromethane and methanol (50 mL). It was neutralized over a carbonate resin (2 equiv) with gentle shaking for 20 hours. The reaction mixture was filtered and the filtrate was evaporated to yield 2-(dimethylamino)acetamide (0.740 g, 100% yield) as a peach-colored solid. $^1$H NMR (400 MHz, DMSO-d$_6$): δ 7.34 (s, 1H), 7.19 (s, 1H), 3.01 (s, 2H), 2.31 (s, 6H).

2-(Dimethylamino)acetamide (0.100 g, 0.974 mmol), N-(4-(2-chloropyridin-4-yloxy)-2,5-difluorophenyl)-N'-(4-fluorophenyl)cyclopropane-1,1-dicarboxamide (0.15 g, 0.325 mmol) (as prepared in Example 1), cesium carbonate (0.159 g, 0.487 mmol), and xantphos (0.018 g, 0.032 mmol) were combined in dry dioxane (2.5 mL) and argon was bubbled through the mixture for 5 minutes. Palladium acetate (5.47 mg, 0.024 mmol) was added and the solution was degassed for an additional 5 minutes. The reaction flask was fitted with a reflux condenser and a balloon of argon and heated at 100° C. for 15 hours. The mixture was cooled to room temperature and then diluted with ethyl acetate (75 mL) and water (45 mL). The water layer was removed and extracted again with ethyl acetate (25 mL). The combined organic layers were washed with brine (50 mL) and dried over magnesium sulfate. Evaporation of the solvent yielded a lavender-colored oil which was purified by silica gel chromatography (0 to 7% methanol in dichloromethane) to give N-(4-(2-(2-(dimethylamino)acetamido)pyridin-4-yloxy)-2,5-difluorophenyl)-N'-(4-fluorophenyl)cyclopropane-1,1-dicarboxamide (0.0823 g, 48% yield). $^1$H NMR (400 MHz, DMSO-d$_6$): δ 11.02 (s, 1H), 9.97 (s, 1H), 9.79 (s, 1H), 8.20 (d, 1H), 8.09 (dd, 1H), 7.65 (d, 1H), 7.57 (m, 3H), 7.16 (m, 2H), 6.76 (dd, 1H), 3.06 (s, 2H), 2.25 (s, 6H), 1.63 (m, 2H), 1.57 (m, 2H); MS (ESI) ink: 528.2 (M+H$^+$).

Example 5

To a solution of Example A3 (300 mg, 1.07 mmol) and 1-(4-fluoro-phenylcarbamoyl)-cyclopropanecarboxylic acid (240 mg, 1.07 mmol) (as prepared in Example B1) in DMF (20 mL) was added HATU (440 mg, 3.2 mmol) and DIEA (280 mg, 2.1 mmol) in portions. The reaction mixture was stirred at 60° C. under nitrogen overnight. After cooling to room temperature water (30 mL) was added and the solution was extracted with ethyl acetate (3×50 mL). The combined organics were washed with brine (3×50 mL), dried over sodium sulfate, and concentrated. The crude product was purified by preparative HPLC to give N-(4-(2-acetamidopyrimidin-4-yloxy)-2,5-difluorophenyl)-N'-(4-fluorophenyl) cyclopropane-1,1-dicarboxamide (42 mg, 8% yield) as a white solid. $^1$HNMR (300 MHz, DMSO-d$_6$): δ 10.95 (s, 1H), 10.40 (s, 1H), 9.75 (s, 1H), 8.49-8.51 (d, J=5.7 Hz, 1H), 7.94-8.01 (dd, J=12.3 Hz, J=8.1 Hz, 1H), 7.48-7.60 (m, 3H), 7.05-7.16 (m, 2H), 6.83-6.84 (d, J=5.4 Hz, 1H), 1.92 (s, 3H), 1.53-1.59 (d, J=19.2 Hz, 4H).

Example 6

N-(4-(2-Chloropyridin-4-yloxy)-2,5-difluorophenyl)-N'-(4-fluorophenyl)cyclopropane-1,1-dicarboxamide (0.25 g, 0.541 mmol) (as prepared in Example 1), cyclopropanecarboxamide (0.092 g, 1.083 mmol), xantphos (0.014 g, 0.024 mmol), and cesium carbonate (0.265 g, 0.812 mmol) were dissolved in dry dioxane (5.41 mL) and argon was bubbled through the mixture for 5 minutes. Pd$_2$(dba)$_3$ (7.44 mg, 0.00812 mmol) was added and additional argon was bubbled through the system. It was then fitted with a reflux condenser and a balloon of argon and heated at 100° C. for 20 hours. The reaction mixture was cooled to room temperature and then partitioned between water (40 mL) and ethyl acetate (70 mL). The layers were separated and the organic layer was washed with brine (50 mL), dried over magnesium sulfate, and evaporated to yield a peach-colored solid. It was stirred in dichloromethane (10 mL) and a cream-colored solid was collected by suction filtration and washed with additional dichloromethane to yield N-(4-(2-(cyclopropanecarboxamido)pyridin-4-yloxy)-2,5-difluorophenyl)-N'-(4-fluorophenyl)cyclopropane-1,1-dicarboxamide (0.238 g, 86% yield). $^1$H NMR (400 MHz, DMSO-d$_6$): δ 11.00 (s, 1H), 10.89 (s, 1H), 9.79 (s, 1H), 8.20 (d, 1H), 8.07 (dd, 1H), 7.63 (d, 1H), 7.56 (m, 3H), 7.16 (m, 2H), 6.74 (dd, 1H), 1.95 (quintet, 1H), 1.62 (m, 2H), 1.56 (m, 2H), 0.75 (m, 4H); MS (ESI) m/z: 511.1 (m+H$^+$).

Example 7

N-(4-(2-Chloropyridin-4-yloxy)-2,5-difluorophenyl)-N'-(4-fluorophenyl)cyclopropane-1,1-dicarboxamide (200 mg, 0.43 mmol) (as prepared in Example 1), propionamide (95 mg, 1.30 mmol), xantphos (25 mg, 0.043 mmol), and cesium carbonate (280 mg, 0.86 mmol) were dissolved in dry dioxane (3 mL) and argon was bubbled through the mixture for 10 minutes. Pd$_2$(dba)$_3$ (20 mg, 0.022 mmol) was then added, and the solution was degassed for an additional 10 minutes. The flask was fitted with a balloon of N$_2$ and slowly heated to 100° C. and stirred overnight. The reaction mixture was cooled to room temperature and diluted with a 4:1 mixture of ethyl acetate and THF (60 mL) and water (40 mL). The organic layer was separated and washed with brine and the aqueous layer was back extracted with the ethyl acetate/THF solution, which was then extracted with brine. The combined organic layers were dried over sodium sulfate and evaporated and the residue was purified by silica gel chromatography to give N-(2,5-difluoro-4-(2-propionamidopyridin-4-yloxy)phenyl)-N'-(4-fluorophenyl)cyclopropane-1,1-dicarboxamide (130 mg, 60.7% yield). $^1$H-NMR (400 MHz, DMSO-d$_6$): δ 11.00 (s, 1H), 10.52 (s, 1H), 9.79 (s, 1H), 8.19 (d, 5.6 Hz, 1H), 8.10-8.05 (m, 1H), 7.66 (d, J=2.4 Hz, 1H), 7.59-7.53 (m, 3H), 7.16 (t, J=8.8 Hz, 2H), 6.74-6.72 (m, 1H), 2.33 (q, 0.7=7.2 Hz, 2H), 1.64-1.55 (m, 4H), 0.99 (t, J=7.2 Hz, 3H).

Example 8

Reference Compound E 1-((4-Fluorophenyl)carbamoyl)cyclopropanecarboxylic acid (see Example B1, 171 mg, 0.77 mmol), N-(4-methoxybenzyl)-4-(4-amino-3-fluorophenoxy)pyridin-2-amine (see PCT Publication No. WO 2008/046003, 200 mg, 0.59 mmol), TBTU (284 mg, 0.88 mol) and DIEA (0.12 ml, 0.73 mmol) were combined in DMF (1.5 mL) and the resultant mixture was stirred overnight. The reaction mixture was partitioned between saturated aqueous NaHCO$_3$ (20 mL) and EtOAc (20 mL). The organic was washed with water (10 mL), brine (10 mL), and 5% aqueous lithium chloride solution (10 mL), and was then dried over MgSO$_4$ and concentrated in vacuo. Dichloromethane was added to the residue and the resultant slurry was filtered. The collected precipitate was washed with CH$_2$Cl$_2$ and dried in vacuo to provide N-(4-(2-(4-methoxybenzylamino)pyridin-4-yloxy)-2-fluorophenyl)-N'-(4-fluorophenyl)cyclopropane-1,1-dicarboxamide (137 mg) as a white solid. The filtrate was concentrated and a second crop (46 mg, total yield 57%) was collected. MS (ESI) m/z: 545.1 (M+H$^+$).

A mixture of N-(4-(2-(4-methoxybenzylamino)pyridin-4-yloxy)-2-fluorophenyl)-N'-(4-fluorophenyl)cyclopropane-1,1-dicarboxamide (160 mg, 0.29 mmol) in CH$_2$Cl$_2$ (0.2 mL) was treated with trifluoroacetic acid (0.4 mL, 5.26 mmol) and the resultant mixture was stirred overnight at RT. The reaction mixture was concentrated to dryness and the residue was purified by reverse-phase silica gel chromatography (25-95% acetonitrile in water, 0.1% TFA). The desired fractions were partitioned between saturated aqueous NaHCO$_3$ and EtOAc. The organics were washed with saturated aqueous NaHCO$_3$, water, and brine and were dried over Na$_2$SO$_4$ and concentrated in vacuo to provide N-(4-(2-aminopyridin-4-yloxy)-2-fluorophenyl)-N'-(4-fluorophenyl)cyclopropane-1,1-dicarboxamide (52 mg, 39% yield). MS (ESI) m/z: 425.1 (M+H$^+$).

A solution of N-(4-(2-aminopyridin-4-yloxy)-2-fluorophenyl)-N'-(4-fluorophenyl)cyclopropane-1,1-dicarboxamide (61 mg, 0.14 mmol) in CH$_2$Cl$_2$ (3 mL) was treated with pyridine (0.058 mL, 0.72 mmol) and acetic anhydride (0.13 mL, 1.4 mmol). The resultant mixture was stirred at RT for 2 days. The reaction was quenched with saturated aqueous NaHCO$_3$ and was further stirred for 2 h. The mixture was diluted with EtOAc (30 mL) and was washed with saturated aqueous NaHCO$_3$ (20 mL), water (20 mL) and brine (20 mL). The mixture was concentrated in vacuo and purified by silica gel chromatography to provide N-(4-(2-acetamidopyridin-4-yloxy)-2-fluorophenyl)-N'-(4-fluorophenyl)cyclopropane-1,1-dicarboxamide (46 mg, 69% yield). $^1$H NMR (400 MHz, DMSO-d$_6$): δ10.56 (s, 1H), 10.54 (s, 1H), 9.96 (s, 1H), 8.18 (d, J=5.8 Hz, 1H), 7.92 (t, 1H), 7.65 (d, J=1.9 Hz, 1H) 7.59 (m, 2H), 7.24 (dd, J=11.2, 2.5 Hz, 1H), 7.15 (m, 2H), 7.01 (m, 1H), 6.68 (dd, J=5.7, 2.3 Hz, 1H), 2.02 (s, 3H), 1.60-1.52 (m, 4H); MS (ESI) m/z: 467.2 (M+H$^+$).

Example 9

N-(4-(2-Chloropyridin-4-yloxy)-2,5-difluorophenyl)-N'-(4-fluorophenyl)cyclopropane-1,1-dicarboxamide (3 g, 6.5 mmol) (as prepared in Example 1), tert-butyl carbamate (2.3 g, 19.5 mmol), Xantphos (0.37 g, 0.65 mmol), and cesium carbonate (4.2 g, 13 mmol) were dissolved in dry dioxane (50 mL) and argon was bubbled through the mixture for 10 minutes. Pd$_2$(dba)$_3$ (0.3 g, 0.33 mmol) was then added, and the solution was sparged with argon for an additional 10 minutes. The flask was fitted with a reflux condenser and a balloon of argon and slowly heated to 100° C. and stirred overnight. The reaction mixture was cooled to RT. It was diluted with ethyl acetate (100 mL) and water (80 mL). The organic layer was separated and washed with brine. The aqueous layer was back extracted with the ethyl acetate, which was then washed with brine. The combined organic layers were dried over sodium sulfate and evaporated. The residue was purified by silica gel chromatography to give tert-butyl 4-(2,5-difluoro-4-(1-(4-fluorophenylcarbamoyl)cyclopropanecarboxamido)phenoxy)pyridin-2-ylcarbamate (1.8 g, 51% yield). $^1$H NMR (400 MHz, DMSO-d$_6$): δ 11.03 (s, 1H), 9.88 (s, 1H), 9.78 (s, 1H), 8.13-8.05 (m, 2H), 7.59-7.53 (m, 3H), 7.33 (d, J=2.4 Hz, 1H), 7.18-7.13 (m, 2H), 6.63 (d, J=2.4 Hz, 1H), 1.63-1.62 (m, 2H), 1.58-1.56 (m, 2H), 1.40 (s, 9H).

To a solution of tert-butyl 4-(2,5-difluoro-4-(1-(4-fluorophenylcarbamoyl)cyclopropanecarboxamido)phenoxy) pyridin-2-ylcarbamate (1.8 g, 3.3 mmol) in CH$_2$Cl$_2$ (100 mL) was added TFA (5 mL) and the mixture was stirred at room temperature overnight. The reaction mixture was adjusted to pH>7 with saturated NaHCO$_3$ solution and the separated organic layer was washed with brine, dried over Na$_2$SO$_4$ and concentrated under reduced pressure to give N-(4-((2-aminopyridin-4-yl)oxy)-2,5-difluorophenyl)-N'-(4-fluorophenyl)cyclopropane-1,1-dicarboxamide (1.2 g, yield 82% yield). $^1$H-NMR (400 MHz, DMSO-d$_6$): δ 10.99 (s, 1H), 9.76 (s, 1H), 8.04 (dd, J=12.4, 7.6 Hz, 1H), 7.79 (d, J=6.0 Hz, 1H), 7.58-7.55 (m, 2H), 7.47 (dd, J=10.8, 7.2 Hz, 1H), 7.16 (t, J=8.8 Hz, 2H), 6.16 (dd, J=6.0, 2.4 Hz, 1H), 6.00 (br s, 2H), 5.81 (d, J=2.0 Hz, 1H), 1.65-1.62 (m, 2H), 1.56-1.53 (m, 2H); MS (ESI): m/z 443.1 [M+H]$^+$.

To a solution of N-(4-((2-aminopyridin-4-yl)oxy)-2,5-difluorophenyl)-N'-(4-fluorophenyl)cyclopropane-1,1-dicarboxamide (130 mg, 0.29 mmol) in 10 mL, of anhydrous tetrahydrofuran was added diisopropylethylamine (75 mg, 0.58 mmol). A solution of methoxyacetyl chloride (34.5 mg, 0.32 mmol) in THF (1 mL) was added drop wise at 0° C. The resultant reaction mixture was stirred at R.T. for 0.5 h. It was diluted with ethyl acetate, washed with brine, dried over sodium sulfate and concentrated. The residue was purified by prep-TLC to give N-(2,5-difluoro-4-((2-(2-methoxyacetamido)pyridin-4-yl)oxy)phenyl)-N'-(4-fluorophenyl)cyclopropane-1,1-dicarboxamide (75 mg, 50% yield). $^1$H NMR (400 MHz, CDCl$_3$): δ 9.79 (s, 1H), 8.89 (s, 1H), 8.53 (s, 1H), 8.30 (d, J=12.0, 7.2 Hz, 1H), 8.17 (d, J=5.6 Hz, 1H), 7.83 (d, J=2.4 Hz, 1H), 7.49-7.45 (m, 2H), 7.07-6.99 (m, 3H), 6.64 (dd, J=5.6, 2.4 Hz 1H), 3.98 (s, 2H), 3.49 (s, 3H), 1.78-1.66 (m, 4H); MS (ESI): m/z 515.2 [M+H]$^+$.

Example 10

In degassed dioxane (5 mL) was placed N-(4-(2-chloropyridin-4-yloxy)-2,5-difluorophenyl)-N-(4-fluorophenyl)cyclopropane-1,1-dicarboxamide (250 mg, 0541 mmol) (as prepared in Example 1), cesium carbonate (353 mg, 1.083 mmol), isobutylamide (236 mg, 2.71 mmol) and xantphos (31 mg, 54 µmol). To this was added tris(dibenzylideneacetone) dipalladium(0) (25 mg, 27 µmol). The mix was warmed to 100° C. overnight. The mixture was cooled to room temperature and diluted with ethyl acetate (30 mL) and filtered to remove solids. The filtrate was washed with aq NaHCO$_3$ (30 mL) and brine (30 mL). The organic phase was dried over Na$_2$SO$_4$ and evaporated at reduced pressure to give a foam. The foam was purified by reverse phase silica gel chromatography (35-80% acetonitrile/water/0.1% TFA). Fractions containing product were combined and evaporated at reduced pressure. The resultant aqueous mixture was then treated with saturated aq NaHCO$_3$ (4 mL) and allowed to stand. The solid was collected by filtration, washed with water (2×5 mL) and dried on high vacuum line at 80° C. overnight to provide N-(2,5-difluoro-4-(2-isobutyramidopyridin-4-yloxy)phenyl)-N'-(4-fluorophenyl)cyclopropane-1,1-dicarboxamide (116 mg, 41% yield). $^1$H NMR (400 MHz, DMSO-d$_6$) δ 11.00 (s, 1H), 10.53 (s, 1H), 9.78 (s, 1H), 8.19 (d, 1H), 8.06-8.10 (m, 1H), 7.66 (s, 1H), 7.60-7.53 (m, 3H), 7.15 (t, 2H), 6.75-6.73 (m, 1H), 2.68 (m, 1H), 1.62-1.51 (m, 4H), 1.00 (d, 6H); MS (ES-API) m/z: 513.2 (M+H$^+$).

Example 11

To a solution of N-(4-((2-aminopyridin-4-yl)oxy)-2,5-difluorophenyl)-N'-(4-fluorophenyl)cyclopropane-1,1-dicarboxamide (150 mg, 0.34 mmol) (as prepared in Example 9) and 2-cyanoacetic acid (44 mg, 0.51 mmol) in DMF (2 mL) was added HATU (258 mg, 0.68 mmol) and DIEA (130 mg, 1 mmol) and the mixture was stirred at 60° C. under nitrogen overnight. The reaction mixture was cooled to room temperature, diluted with ethyl acetate (50 mL) and H$_2$O (50 mL) and the organic layer was washed with brine, dried and concentrated under reduced pressure. The residue was purified by prep-TLC to give N-(4-(2-(2-cyanoacetamido)pyridin-4-yloxy)-2,5-difluorophenyl)-N'-(4-fluorophenyl)cyclopropane-1,1-dicarboxamide (70 mg, yield 64.5%). $^1$H-NMR (400 MHz, DMSO-d$_6$): δ 10.99 (s, 1H), 10.94 (s, 1H), 9.81 (s, 1H), 8.23 (d, J=5.6 Hz, 1H), 8.08 (dd, J=12.4, 6.8 Hz, 1H), 7.59-7.55 (m, 4H), 7.15 (t, J=8.8 Hz, 2H), 6.80 (dd, J=6.0, 2.4 Hz, 1H), 3.92 (s, 2H), 1.61-1.56 (m, 4H); MS (ESI): m/z 510.2 [M+H]$^+$.

Example 12

To a solution of N-(4-((2-aminopyridin-4-yl)oxy)-2,5-difluorophenyl)-N'-(4-fluorophenyl)cyclopropane-1,1-dicarboxamide (440 mg, 1 mmol) (as prepared in Example 9) and 1-(tert-butoxycarbonyl) azetidine-3-carboxylic acid (402 mg, 2 mmol) in DMF (5 mL) was added HATU (1.1 g, 3 mmol), followed by DIEA (516 mg, 4 mmol). The mixture was sparged with nitrogen and then stirred 50° C. overnight. The reaction mixture was partitioned between ethyl acetate and water. The organic layer was washed with brine, dried over sodium sulfate and concentrated under reduced pressure. The residue was purified by column on a silica gel chromatography to give tert-butyl 3-(4-(2,5-difluoro-4-(1-(4-fluorophenylcarbamoyl)cyclopropanecarboxamido)phenoxy) pyridin-2-ylcarbamoyl)azetidine-1-carboxylate (250 mg, 40% yield). $^1$H-NMR (400 MHz, DMSO-d$_6$): δ 11.01 (s, 1H), 10.72 (s, 1H), 9.79 (s, 1H), 8.19 (d, J=5.6 Hz, 1H), 8.10-8.05 (m, 1H), 7.66 (s, 1H), 7.58-7.53 (m, 3H), 7.14 (t, J=8.8 Hz, 2H), 6.77-6.75 (m, 1H), 3.90-3.84 (m, 4H), 3.55-5.53 (m, 1H), 1.63-1.53 (m, 4H), 1.33 (s, 9H).

To a solution of tert-butyl 3-(4-(2,5-difluoro-4-(1-(4-fluorophenylcarbamoyl)cyclopropanecarboxamido)phenoxy)pyridin-2-ylcarbamoyl)azetidine-1-carboxylate (220 mg, 0.35 mmol) in CH$_2$Cl$_2$ (4 mL) was added TFA (0.2 mL) at 0° C. and the reaction was stirred at room temperature overnight. Saturated NaHCO$_3$ solution was added drop wise until pH>7 and the mixture with extracted with CH$_2$Cl$_2$ (2×50 mL). The combined organic layers were washed with brine, dried over Na$_2$SO$_4$, filtered and concentrated under reduced pressure. The residue was purified by HPLC separation to give N-(4-(2-(azetidine-3-carboxamido)pyridin-4-yloxy)-2,5-difluorophenyl)-N'-(4-fluorophenyl)cyclopropane-1,1-dicarboxamide (16 mg, yield 8.7%). $^1$H-NMR (400 MHz, MeOH-d$_4$): δ 9.50 (s), 8.46 (d, J=7.2 Hz, 1H), 8.33 (dd, J=7.2 Hz, 12.4 Hz, 1H), 7.53-7.43 (m, 3H), 7.26 (dd, J=7.2 Hz, 2.4 Hz, 1H), 7.10 (t, J=8.4 Hz, 2H), 6.75 (d, J=2.4 Hz, 1H), 4.61-4.54 (m, 1H), 3.63-3.58 (m, 1H), 3.49-3.44 (m, 1H), 3.31-3.29 (m, 1H), 3.27-3.25 (m, 1H), 1.75-1.73 (m, 4H); MS (ESI): m/z 443.2 [M+H]$^+$.

Example 13

To a solution of N-(4-(2-chloropyridin-4-yloxy)-2,5-difluorophenyl)-N'-(4-fluorophenyl)cyclopropane-1,1-dicarboxamide (200 mg, 0.45 mmol) (as prepared in Example 9) and cyclobutanecarboxylic acid (90 mg, 0.9 mmol) in DMF (3 ml) was added HATU (513 mg, 1.35 mmol), followed by DIEA (516 mg, 4 mmol). The mixture was sparged with nitrogen and stirred overnight at 60° C. The reaction mixture was partitioned between ethyl acetate and water. The organic layer was washed with brine, dried over sodium sulfate and concentrated under reduced pressure. The residue was purified by silica gel chromatography to give N-(4-(2-(cyclobutanecarboxamido)pyridin-4-yloxy)-2,5-difluorophenyl)-N'-(4-fluorophenyl)cyclopropane-1,1-dicarboxamide (97 mg, yield 41.1%). $^1$H NMR (400 MHz, DMSO-d$_6$): δ 11.02 (s, 1H), 10.42 (s, 1H), 9.80 (s, 1H), 8.18 (d, J=6.0 Hz, 1H), 8.08 (dd, J=12.4, 6.8 Hz, 1H), 7.68 (s, 1H), 7.60-7.54 (m, 3H), 7.17 (t, J=8.8 Hz, 2H), 6.73 (dd, J=5.6, 2.4 Hz, 1H), 2.18-2.02 (m, 4H), 1.92-1.83 (m, 1H), 1.76-7.69 (m, 1H), 1.62-1.55 (m, 4H); MS (ESI): m/z 525.1 [M+H]

Example 14

To a solution of (R)-2-methoxy-propionic acid (300 mg, 2.88 mmol) and N-methylmorpholine (432 mg, 4.32 mmol) in anhydrous CH$_2$Cl$_2$ was added drop wise isobutyl chloroformate (588 mg, 4.32 mmol). The resultant mixture was stirred at RT for 1 h. N-(4-(2-Chloropyridin-4-yloxy)-2,5-difluorophenyl)-N'-(4-fluorophenyl)cyclopropane-1,1-dicarboxamide (200 mg, 0.452 mmol) was added and the resulting mixture was stirred at RT for 12 h. The reaction mixture was concentrated under vacuo and purified by HPLC separation to give (R)—N-(2,5-difluoro-4-((2-(2-methoxypropanamido)pyridin-4-yl)oxy)phenyl)-N'-(4-fluorophenyl)cyclopropane-1,1-dicarboxamide (50 mg, 21%). $^1$H NMR (400 MHz, CDCl$_3$): δ 9.79 (s, 1H), 9.07 (s, 1H), 8.51 (s, 1H), 8.32-8.27 (m, 1H), 8.16 (d, J=5.6 Hz, 1H), 7.83 (d, J=2 Hz, 1H), 7.48-7.44 (m, 2H), 7.06-6.98 (m, 3H), 6.66-6.64 (m, 1H), 3.82 (q, J=6.8 Hz, 1H), 3.50 (s, 3H), 1.75-1.67 (m. 4H), 1.42 (d, J=6.8 Hz, 3H); MS (ESI): m/z 529.1[M+H]$^+$.

Example 15

To a solution of (R)-2-benzyloxy-propionic acid (500 mg, 2.78 mmol) and N-methylmorpholine (416 mg, 4.16 mmol) in anhydrous CH$_2$Cl$_2$ was added isobutyl chloroformate (566 mg, 4.32 mmol) dropwise. The mixture was stirred at 25° C. for 1 h. N-(4-((2-aminopyridin-4-yl)oxy)-2,5-difluorophenyl)-N'-(4-fluorophenyl)cyclopropane-1,1-dicarboxamide (200 mg, 0.452 mmol) was added and the resulting mixture was stirred at 25° C. for 12 h. The reaction mixture was concentrated in vacuo to give (R)—N-(4-((2-(2-(benzyloxy)propanamido)pyridin-4-yl)oxy)-2,5-difluorophenyl)-N'-(4-fluorophenyl)cyclopropane-1,1-dicarboxamide (200 mg, 71.5%). It was used without further purification.

To a solution of (R)—N-(4-((2-(2-(benzyloxy)propanamido)pyridin-4-yl)oxy)-2,5-difluorophenyl)-N'-(4-fluorophenyl)cyclopropane-1,1-dicarboxamide (200 mg, 0.331 mmol) in methanol (20 mL) was added Pd(OH)$_2$ (50 mg). The mixture was then hydrogenated (1 atm) for 12 h. The reaction mixture was filtered, concentrated and purified by HPLC chromatography to give (R)—N-(2,5-difluoro-4-((2-(2-hydroxypropanamido)pyridin-4-yl)oxy)phenyl)-N'-(4-fluorophenyl)cyclopropane-1,1-dicarboxamide (20 mg, 11.7% yield). $^1$H NMR (400 MHz, CD$_3$OD): δ 8.23-8.18 (m, 2H), 7.69 (s, 1H), 7.54-7.50 (m, 2H), 7.31-7.28 (m, 1H), 7.09-7.05 (m, 2H), 6.86-6.84 (m, 1H), 4.28-4.23 (q, J=6.8 Hz, 1H), 1.76-1.67 (m, 4H), 1.39 (d, J=6.8 Hz, 3H); MS (ESI); m/z 515.1 [M+H]$^+$ Example 16

N-(4-(2-chloropyridin-4-yloxy)-2,5-difluorophenyl)-N'-(4-fluorophenyl)cyclopropane-1,1-dicarboxamide (160 mg, 0.34 mmol) (as prepared in Example 1), 2,2-dimethyl-propionamide (100 mg, 1 mmol), xantphos (40 mg, 0.068 mmol), and cesium carbonate (222 mg, 0.68 mmol) were dissolved in dry dioxane (2 mL) and argon was bubbled through the mixture for 10 minutes. Pd(OAc)$_2$ (8 mg, 0.034 mmol) was then added, and the solution was degassed for an additional 10 minutes. The mixture was heated to 100° C. and stirred overnight. The reaction mixture was cooled to RT and diluted with EtOAc (20 mL) and water (15 mL). The organic layer was separated and washed with brine. The aqueous layer was extracted with EtOAc and the extracts were washed with brine. The combined organic layers were dried over sodium sulfate and concentrated in vacuo. The residue was purified by prep-TLC to give N-(2,5-difluoro-4-((2-pivalamidopyridin-4-yl)oxy)phenyl)-N'-(4-fluorophenyl)cyclopropane-1,1-dicarboxamide (72 mg, 40% yield). $^1$H-NMR (400 MHz, DMSO-d$_6$): δ 8.19-8.17 (m, 2H), 7.69 (s, 1H), 7.53-7.51 (m, 2H), 7.24 (br t, J=7.2 Hz, 1H), 7.10-7.05 (m, 2H), 6.73 (brs, 1H), 1.73-1.69 (m, 4H), 1.27 (s, 9H); MS (ESI); m/z 527.3 [M+H]$^+$.

Example 17

To a solution of (S)-2-methoxy-propionic acid (400 mg, 3.84 mmol) and N-methylmorpholine (577 mg, 5.77 mmol) in anhydrous CH$_2$Cl$_2$ was added drop wise isobutyl chloroformate (773 mg, 5.77 mmol) and the resultant mixture was stirred at 25° C. for 1 h. N-(4-((2-aminopyridin-4-yl)oxy)-2,5-difluorophenyl)-N'-(4-fluorophenyl)cyclopropane-1,1-dicarboxamide (200 mg, 0.452 mmol) was added to the mixture. The result mixture was stirred at 25° C. for 12 h. The reaction mixture was concentrated under reduced pressure and purified by HPLC chromatography to give (S)—N-(2,5-difluoro-4-((2-(2-methoxypropanamido)pyridin-4-yl)oxy)

phenyl)-N-(4-fluorophenyl)cyclopropane-1,1-dicarboxamide (50 mg, 21% yield). $^1$H NMR (400 MHz, Methanol-d$_4$): δ: 8.21-8.16 (m, 2H), 7.65 (d, J=2.4 Hz, 1H), 7.55-7.51 (m, 2H), 7.26 (dd, =10.4, 6.8 Hz, 1H), 7.10-7.05 (m, 2H), 6.76 (q, J=5.6, 2.4 Hz, 1H), 3.90 (q, J=6.8 Hz, 1H), 3.44, (s, 3H), 1.74-1.69 (m, 4H), 1.38 (d, J=6.8 Hz, 3H) [missing 3 NH]; MS (ESI): m/z 528.9 [M+H]$^+$.

Example 18

To a solution of (S)-2-Acetoxy-propionic acid (300 mg, 2.278 mmol) and N-methylmorpholine (341 mg, 3.41 mmol) in anhydrous CH$_2$Cl$_2$ was added drop wise isobutyl chloroformate (457 mg, 3.41 mmol). The resultant mixture was stirred at 25° C. for 1 h. N-(4-((2-aminopyridin-4-yl)oxy)-2,5-difluorophenyl)-N'-(4-fluorophenyl)cyclopropane-1,1-dicarboxamide (250 mg, 0.578 mmol) was added and the resulting mixture was stirred at 25° C. for 12 h. The reaction mixture was concentrated under reduced pressure to give (S)-1-((4-(2,5-difluoro-4-(1-((4-fluorophenyl)carbamoyl)cyclopropanecarboxamido)phenoxy)pyridin-2-yl)amino)-1-oxopropan-2-yl acetate (180 mg, 55.9% yield) which was without further purification.

To a solution of (S)-1-((4-(2,5-difluoro-4-(1-((4-fluorophenyl)carbamoyl)cyclopropanecarboxamido)phenoxy)pyridin-2-yl)amino)-1-oxopropan-2-yl acetate (180 mg, 0.323 mmol) in a solution of MeOH—H$_2$O (3:1, 20 mL) was added potassium carbonate (111.6 mg, 0.809 mmol), the mixture was stirred at 25° C. for 12 h. The reaction mixture was concentrated and purified by prep-TLC to give (S)—N-(2,5-difluoro-4-((2-(2-hydroxypropanamido)pyridin-4-yl)oxy)phenyl)-N'-(4-fluorophenyl)cyclopropane-1,1-dicarboxamide (100 mg, 60% yield). $^1$H NMR (400 MHz, Methanol-d$_4$): δ 8.21-8.16 (m. 2H), 7.78 (d, J=2.4 Hz, 1H), 7.54-7.51 (m, 2H), 7.28-7.24 (m, 1H), 7.10-7.05 (m, 2H), 6.76-6.74 (dd, J=6.0, 2.4 Hz, 1H), 4.23 (q, J=6.8 Hz, 1H), 1.75-1.67 (m, 4H), 1.39 (d, J=6.8 Hz, 3H); MS (ESI): m/z 515.2 [M+H]$^+$.

Example 19

To a solution of N-(4-((2-aminopyridin-4-yl)oxy)-2,5-difluorophenyl)-N'-(4-fluorophenyl)cyclopropane-1,1-dicarboxamide (250 mg, 0.565 mmol) and 2-fluoro-2-methylpropanoic acid (108 mg, 1.02 mmol) in anhydrous CH$_2$Cl$_2$ (30 mL) was added HATU (323 mg, 0.85 mmol) and DIPEA (2.5 mL) under N$_2$. This reaction mixture was stirred at room temperature overnight. The solvent was removed in vacuo. The residue was poured into water (100 mL), extracted with ethyl acetate (3×50 mL), washed with brine, dried over anhydrous sodium sulfate and concentrated in vacuo. This crude product was purified by silica gel chromatography to give N-(2,5-difluoro-4-((2-(2-fluoro-2-methylpropanamido)pyridin-4-yl)oxy)phenyl)-N'-(4-fluorophenyl)cyclopropane-1,1-dicarboxamide (128 mg, 43% yield). $^1$H-NMR (400 MHz, Methanol-d$_4$): δ 8.21-8.17 (m, 2H), 7.73 (d, J=2.4 Hz, 1H), 7.54-7.51 (m, 2H), 7.23 (dd, J=10.8, 7.2 Hz, 1H), 7.08-7.04 (m, 2H), 6.75 (dd, J=5.6, 2.4 Hz, 1H), 1.76-1.69 (m, 4H), 1.62 (s, 3H), 1.56 (s, 3H); MS (ESI): m/z 531.1 [M+H]$^+$.

Biological Data c-MET Kinase Assay

Activity of c-MET kinase (Seq. ID No. 2) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 µl) contained c-MET (c-MET residues: 956-1390, from Invitrogen, catalogue #PV3143, 6 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octyl-glucoside and 1% DMSO, 7.5. Test compounds were incubated with c-MET (Seq. ID No. 2) and other reaction reagents at 22° C. for 0.5 h before ATP (100 µM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

c-MET Kinase
(Seq ID No. 2)
MSYYHHHHHHDYDIPTTENLYFQGAMLVPRGSPWIPFTMKKRKQIKDLGS

ELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAV

QHVVIGPSSLIVHFNEVIGRGHFGCVYHGTLLDNDGKKIHCAVKSLNRIT

DIGEVSQFLTEGIIMKDFSHPNVLSLLGICLRSEGSPLVVLPYMKHGDLR

NFIRNETHNPTVKDLIGFGLQVAKGMKYLASKKFVHRDLAARNCMLDEKF

TVKVADFGLARDMYDKEYYSVHNKTGAKLPVKWMALESLQTQKFTTKSDV

WSFGVLLWELMTRGAPPYPDVNTFDITVYLLQGRRLLQPEYCPDPLYEVM

LKCWHPKAEMRPSFSELVSRISAIFSTFIGEHYVHVNATYVNVKCVAPYP

SLLSSEDNADDEVDTRPASFWETS.

c-KIT Kinase Assay

Activity of c-KIT kinase (Seq. ID No. 1) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 µl) contained c-KIT (cKIT residues T544-V976, from ProQinase, 5.4 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with c-KIT (Seq. ID No. 1) and other reaction reagents at 22° C. for less than 2 min before ATP (200 µM) was added to start the reaction. The absorption at 340 nm was monitored continuously for 0.5 hours at 30° C. on Polarstar Optima plate reader (BMG). The reaction rate was calculated using the 0 to 0.5 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

c-KIT with N-terminal GST fusion (Seq ID No. 1)

LGYWKIKGLVQPTRLLLEYLEEKYEEHLYERDEGDKWRNKKFELGLEFPN

LPYYIDGDVKLIQSMAIIRYIADKHNMLGGCPKERAEISMLEGAVDIRYG

VSRIAYSKDFETLKVDFLSKLPEMLKMFEDRLCHKTYLNGDHVTHPDFML

YDALDVVLYMDPMCLDAFPKLVCFKKRIEAIPQIDKYLKSSKYIWPLQGW

QATFGGGDHPPKSDLVPRHNQTSLYKKAGSAAAVLEENLYFQGTYKYLQK

PMYEVQWKVVEEINGNNYVYIDPTQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV.

KDR Kinase Assay

Assay K1

The activity of KDR kinase was determined by following the production of ADP from the kinase reaction through coupling with the pyruvate kinase/lactate dehydrogenase system (e.g., Schindler et al. Science 2000, 289, pp. 1938-1942). In this assay, the oxidation of NADH (thus the decrease at A340 nm) was continuously monitored spectrophotometrically. The reaction mixture (100 µl) contained KDR (Seq ID No. 3, 1.5 nM to 7.1 nM, nominal concentration), polyE4Y (1 mg/mL), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM $MgCl_2$, 6.8 mM DTT, and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG) or instrument of similar capacity. The reaction rate was calculated using the 1 h to 2 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was employed (2) the reaction was pre-incubated at 30° C. for 2 h prior to initiation with ATP and (3) 1.0 mM ATP (final concentration) was used to initiate the reaction.

Assay K3

KDR kinase assay K3 is the same as for assay K1 except that (1) a nominal concentration of 1.1 nM of enzyme was employed, (2) the buffer components per 100 µl reaction mixture were as follows: 75 mM Tris buffer containing 0.066% octyl-glucoside, 17 mM $MgCl_2$, and 1% DMSO at pH 7.5, (3) the final concentration of DTT was 0.66 mM, (4) the reaction was pre-incubated at 30° C. for 1 h prior to initiation with ATP, and (5) 1.0 mM ATP (final concentration) was used to initiate the reaction.

KDR protein sequence used for screening (Seq. ID No. 3)

DPDELPLDEHCERLPYDASKWEFPRDRLKLGKPLGRGAFGQVIEADAFGI

DKTATCRTVAVKMLKEGATHSEHRALMSELKILIHIGHHLNVVNLLGACT

KPGGPLMVIVEFCKFGNLSTYLRSKRNEFVPYKVAPEDLYKDFLTLEHLI

CYSFQVAKGMEFLASRKCIHRDLAARNILLSEKNVVKICDFGLARDIYKD

PDYVRKGDARLPLKWMAPETIFDRVYTIQSDVWSFGVLLWEIFSLGASPY

PGVKIDEEFCRRLKEGTRMRAPDYTTPEMYQTMLDCWHGEPSQRPTFSEL

VEHLGNLLQANAQQD

FMS Kinase Assay

Activity of FMS kinase was determined by following the production of ADP from the kinase reaction through coupling with the pyruvate kinase/lactate dehydrogenase system (e.g. Schindler et al. Science 2000, 289, pp. 1938-1942). In this assay, the oxidation of NADH (thus the decrease at A340 nm) was continuously monitored spectrophotometrically. The reaction mixture (100 µl) contained FMS (purchased from Invitrogen or Millipore, 6 nM), polyE4Y (1 mg/mL), $MgCl_2$ (10 mM), pyruvate kinase (4 units), lactate dehydrogenase (0.7 units), phosphoenol pyruvate (1 mM) and NADH (0.28 mM) and ATP (500 µM) in a 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on a Polarstar Optima or Synergy 2 plate reader. The reaction rate was calculated using the 2 to 3 h time frame. Percent inhibition was obtained by comparison of reaction rate with that of a control (i.e., with no test compound). $IC_{50}$ values were calculated from a series of percent inhibition values determined at a range of inhibitor concentrations using software routine's as implemented in the GraphPad Prism software package.

EBC-1 Cell Culture

EBC-1 cells (catalog #JCRB0820) were obtained from the Japan Health Science Research Resources Bank, Osaka, Japan. Briefly, cells were grown in DMEM supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

EBC-1 Cell Proliferation Assay

A serial dilution of test compound was dispensed into a 96-well black clear bottom plate (Corning, Corning, N.Y.). For each cell line, five thousand cells were added per well in 200 µL complete growth medium. Plates were incubated for 67 hours at 37° C., 5% $CO_2$, 95% humidity. At the end of the incubation period 40 µL of a 440 µM solution of resazurin (Sigma, St. Louis, Mo.) in PBS was added to each well and incubated for an additional 5 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

MKN-45 Cell Culture

MKN-45 cells (catalog #JCRB0254) were obtained from the Japan Health Science Research Resources Bank, Osaka, Japan. Briefly, cells were grown in RPMI 1640 media supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

MKN-45 Cell Proliferation Assay

A serial dilution of test compound was dispensed into a 96-well black clear bottom plate (Corning, Corning, N.Y.). Five thousand cells were added per well in 200 μL complete growth medium. Plates were incubated for 67 hours at 37° C., 5% $CO_2$, 95% humidity. At the end of the incubation period 40 μL of a 440 μM solution of resazurin (Sigma, St. Louis, Mo.) in PBS was added to each well and plates were incubated for an additional 5 h at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

RON Kinase Assay

Activity of RON kinase was determined by a radioactive filtration binding assay where incorporation of $^{33}P$ from $^{33}P$-γ-ATP to the substrate was measured. In this assay, detection of $^{33}P$ was indicative of RON phosphorylation activity which was directly proportional to the amount of phosphorylated peptide substrate (KKSRGDYMTMQIG, SEQ ID NO: 4). Initially, the reaction mixture contained: 400 nM RON, 20 mM HEPES, pH 7.5, 10 mM $MgCl_2$, 2 mM $MnCl_2$, 1 mM EGTA, 0.02% Brij 35, 0.02 mg/mL BSA, 0.1 mM $Na_3VO_4$, and 2 mM DTT. The reaction mixture was incubated with compound at room temperature for 30 minutes. To initiate the reaction, an equal volume of 20 μM ATP and 0.4 mg/mL peptide substrate were added and then incubated at room temperature for 2 hours. The final assay conditions were: 200 nM RON, 10 μM ATP, 0.2 mg/mL substrate 20 mM HEPES, pH 7.5, 10 mM $MgCl_2$, 1 mM EGTA, 0.02% Brij 35, 0.02 mg/mL BSA, 0.1 mM $Na_3VO_4$, 2 mM DTT, and 1% DMSO. $IC_{50}$ values were calculated from a series of % Activity values determined at a range of inhibitor concentrations using software routines as implemented in the GraphPad Prism software package.

RON Sequence/Protein Information (UniProtKB/Swiss-Prot Entry Q04912)

GST tagged recombinant human RON, amino acids 983-1400. Expressed in insect cells.

FLT1 Kinase Assay

Activity of FLT1 kinase was determined by a radioactive filtration binding assay where incorporation of $^{33}P$ from $^{33}P$-γ-ATP to the substrate is measured. In this assay, detection of $^{33}P$ was indicative of FLT1 phosphorylation activity which was directly proportional to the amount of phosphorylated peptide substrate poly[Glu:Tyr] (4:1). Initially, the reaction mixture contained: 400 nM FLT1, 20 mM HEPES, pH 7.5, 10 mM $MgCl_2$, 2 mM $MnCl_2$, 1 mM EGTA, 0.02% Brij 35, 0.02 mg/mL BSA, 0.1 mM $Na_3VO_4$, and 2 mM DTT. The reaction mixture was incubated with compound at room temperature for 30 minutes. To initiate the reaction, an equal volume of 20 μM ATP and 0.2 mg/mL peptide substrate were added and then incubated at room temperature for 2 hours. The final assay conditions were: 200 nM FLT1, 10 μM ATP, 0.1 mg/ml, substrate 20 mM HEPES, pH 7.5, 10 mM $MgCl_2$, 1 mM EGTA, 0.02% Brij 35, 0.02 mg/mL BSA, 0.1 mM $Na_3VO_4$, 2 mM DTT, and 1% DMSO. $IC_{50}$ values were calculated from a series of % Activity values determined at a range of inhibitor concentrations using software routines as implemented in the Graph Pad Prism software package.

FLT1 Sentience/Protein Information (UniProtKB/Swiss-Prot Entry P17948)

GST tagged recombinant human FLT1, amino acids 781-1338. Expressed in insect cells.

RET Kinase Assay

Activity of RET kinase was determined by following the production of ADP from the kinase reaction through coupling with the pyruvate kinase/lactate dehydrogenase system (see e.g., Schindler et al. *Science* (2000) 289: 1938-1942). In this assay, the oxidation of NADH (thus the decrease at A340 nm) was continuously monitored spectrophotometrically. The reaction mixture (100 μl) contained RET (amino acid residues 658-1114, from Invitrogen, 2 nM), polyE4Y (1.5 mg/ml), $MgCl_2$ (18 mM), pyruvate kinase (4 units), lactate dehydrogenase (0.7 units), phosphoenol pyruvate (1 mM), and NADH (0.28 mM) in 90 mM Iris buffer containing 0.2% octyl-glucoside, 1 mM DTT and 1% DMSO, pH 7.5. Test compounds were incubated with RET kinase and other reaction reagents at 22° C. for <2 min before ATP (500 μM) was added to start the reaction. The absorption at 340 nm was monitored continuously for 3 hours at 30° C. on BioTek Synergy 2 Reader. The reaction rate was calculated using the 1 to 2 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

RET Sequence/Protein Information (UniProtKB/Swiss-Prot Entry P07949)

GST tagged recombinant human RET, amino acids 658-1114. Expressed in insect cells.

Compounds, of Formula I exhibit inhibitory activity in one or more of the aforementioned assays when evaluated at concentrations ≤10 μM.

An unexpected increase in potency and/or selectivity is observed when the central phenyl ring of the compounds disclosed herein contains a distinct para-di substitution pattern. In addition, it is theorized that the presence of certain R3 moieties on the monocyclic nitrogen-containing heteroaromatic ring work in concert with the para-di-substitution pattern of the central phenyl ring to unexpectedly give rise to further improvement in potency and/or selectivity. It is theorized that the identity and location of certain moieties on the heteroaromatic ring relative to the ether oxygen linker and a ring nitrogen atom contribute to these results. For example, in the compounds described herein, the NH—R3 moiety is regiochemically located meta- to the ether oxygen linker and ortho- to a ring nitrogen atom.

The unexpected potency and selectivity of compounds having the characteristics of Formula I are exemplified in the data presented in Table 1. Compound F, Compound G, and Compound H are disclosed in U.S. Patent Publication No. 2008/0319188 A1 (hereinafter "'the '188 Application"). The data for Compound F, Compound G, and Compound H are taken from the values published in the '188 application (pp. 96-97) and in U.S. Patent Publication No. 2009/0227556 A1 (hereinafter "the '556 application"). The data for Compound D (Example 1) and Compound E (Example 8) were obtained by the methods described in the Biological Data section, below.

TABLE 1

| Inhibitor | MET IC$_{50}$ | RON IC$_{50}$ | Fold Selectivity RON/MET | RET IC$_{50}$ | Fold Selectivity RET/MET | VEGFR-1 IC$_{50}$ | Fold Selectivity VEGR-1/ MET | VEGFR-2 IC$_{50}$ | Fold Selectivity VEGFR-2/ MET |
|---|---|---|---|---|---|---|---|---|---|
| Compound F | 53 nM | 17 nM | 0.32 | 130 nM | 2.45 | 88 nM | 1.66 | 240 nM | 4.53 |
| Compound G | 47 nM | 2 nM | 0.04 | 38 nM | 0.81 | 21 nM | 0.45 | 100 nM | 2.13 |
| Compound H | 4 nM | 3 nM | 0.75 | 28 nM | 7 | 14 nM | 3.5 | 10 nM | 2.5 |
| Compound D | 4 nM | 5,000 nM | >1,250 | >3,300 nM | >825 | 79 nM | 19.75 | 52 nM | 13 |
| Compound E | 26 nM | 100 nM | 3.85 | 43 nM | 1.65 | 160 nM | 6.15 | 122 nM | 4.69 |

The structures of Compound F, Compound G, Compound H, Compound D, and Compound E are below.

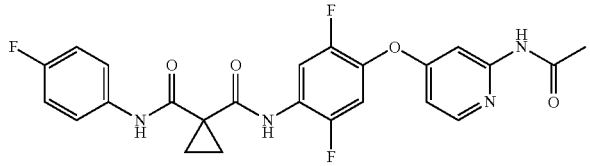

Compound D (Example 1)

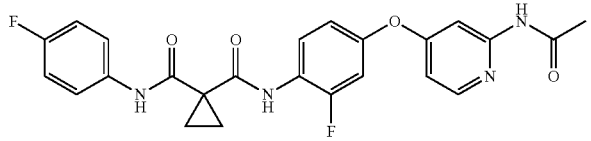

Reference Compound E (Example 8)

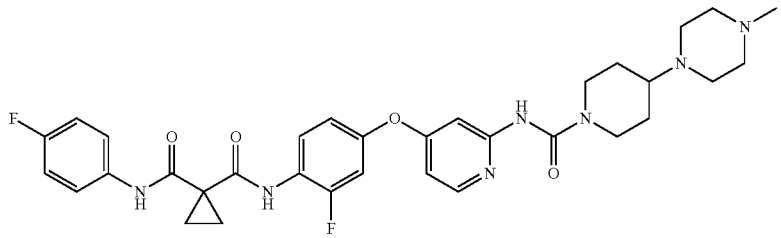

Reference Compound F

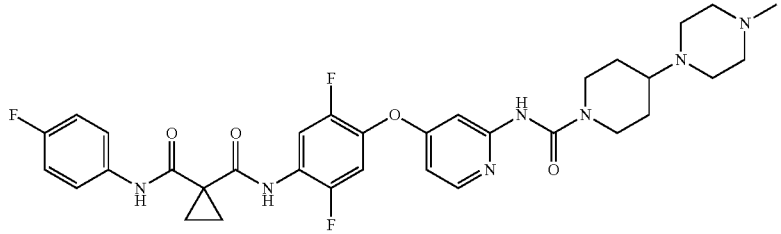

Reference Compound G

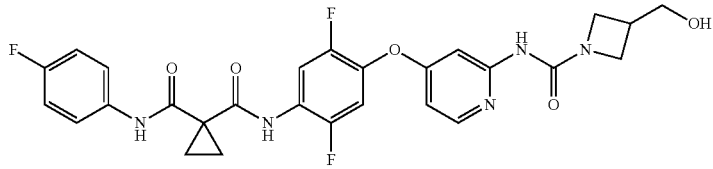

Reference Compound H

Cyclopropane diamide Compound F, Compound G, and Compound H were disclosed in the '188 Application as Examples 15, 92, and 91, respectively. As shown in Table 1, Compound F and Compound G were reported to inhibit MET kinase biochemical activity with comparable IC$_{50}$ values of 53 nM and 47 nM, respectively.

The structures of Compound F and Compound G are almost identical, with the exception that Compound F is mono-fluorinated in the central phenyl ring whereas Compound G is di-fluorinated wherein the two fluorines are oriented para- with respect to each other in the central phenyl ring.

In contrast, it has unexpectedly been found that Compound D, disclosed herein, potently inhibits c-MET kinase with an IC$_{50}$ value of 4 nM. Compound D is 6.5-fold more potent versus c-MET kinase than its mono-fluoro analog Compound E (4 nM versus 26 nM; see Table 1). This 6.5-fold greater potency versus MET kinase is unexpected in view of the c-MET inhibition data for Compound G compared to its corresponding mono-fluoro analog Compound F. As reported in the '188 Application, Compound G and Compound F exhibit essentially equivalent potency versus c-MET kinase (53 nM versus 47 nM, respectively; 1.1-fold ratio of potency). See the '188 application, pp. 96-97. Compound H is also reported to be a potent MET kinase inhibitor, with $IC_{50}$ of 4 nM. Id. Compound H, like Compound D, is di-fluorinated, with the two fluorines being oriented para with respect to each other in the central phenyl ring. Compound H, however, does not exhibit the selectivity against c-MET inhibition that has been observed for Compound D.

It has also been unexpectedly been found that Compound D exhibits a much higher kinase selectivity versus RON, RET, VEGFR-1, and VEGFR-2 kinases, compared to Compound E. See Table 1. RON is a very close kinase of the MET subfamily of kinases, and inhibitors of MET kinase are often not selective versus RON. Whereas Compound D is >1,250 fold selective of MET kinase versus RON kinase, Compound E is only 3.85 fold of MET kinase versus RON kinase. See Table 1. Also, whereas Compound D is >825 fold selective of MET kinase versus RET kinase, Compound E is only 1.65 fold selective of MET kinase versus RET kinase. Additionally, whereas Compound D is 19.75-fold selective of MET kinase versus VEGFR-1 kinase, Compound E is significantly less selective: 6.15-fold selective of MET kinase versus VEGFR-1 kinase. Finally, whereas Compound D is 13-fold selective of MET kinase versus VEGFR-2 kinase, Compound E is significantly less selective: 4.69-fold selective of MET kinase versus VEGFR-2 kinase.

In contrast, as illustrated in Table 1, Compound F, Compound G, and Compound H do not exhibit selectivity of c-MET versus RON kinase, as evidenced by reported $IC_{50}$ values versus RON of 17 nM, 2 nM, and 3 nM, respectively. See Table 1, below and the '556 application, pg. 36. Moreover, as shown in Table 1, the Fold Selectivity of RON relative to MET kinase is 0.32, 0.04, and 0.75, respectively, for Compound F, Compound G, and Compound H, indicating that the compounds are more potent against RON kinase than against MET kinase. In view of these data, the selectivity of Compound D versus these 'off target' kinases is unexpected. In summary, it is theorized that the presence of the central phenyl ring para-di-substitution pattern, in combination with the pyridine ring acetamide moiety, confers this unexpected MET potency and selectivity versus these 'off targets.'

Without wishing to be bound by a particular theory, it is theorized that the presence of certain non-hydrogen R3 moieties on the monocyclic nitrogen-containing heteroaromatic ring work in concert with the para-di-substitution pattern of the central phenyl ring to unexpectedly give rise to further improvement in potency and/or selectivity. Specifically, one difference in the structure of Compound D, Compound G, and Compound H resides in the identity of the substituent in the pyridine ring. In Compound D, this substituent is —NHC(O)CH3 (an acetamide), whereas in Compound G and Compound H the substituent is a more extended urea. In summary, it is theorized that the combination of the presence oldie central phenyl ring para-di-substitution pattern, in combination with the specific pyridine ring moiety (e.g., acetamide vs. extended urea moieties), confers this unexpected c-MET potency and high selectivity versus these 'off targets.' Other features which may also contribute to the unexpected results described herein include: a para-regiochemical relationship between the oxygen ether linker and the nitrogen amide atoms attached to the central phenyl ring; a regiochemical para-relationship between the oxygen ether linker atom and the ring nitrogen in the nitrogen-containing ring; and absence of an alkyl spacer between the aromatic ring and the nitrogen of the cyclopropane carbonyl. While cyclopropane amides have been reported in the literature as inhibitors of c-MET kinase activity, compounds having the features discussed above have not been disclosed.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I,

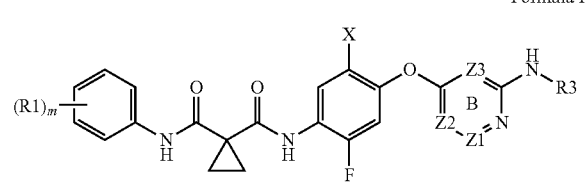

Formula I or a pharmaceutically acceptable salt, enantiomer, stereoisomer, or tautomer thereof,
wherein
X is halogen;
Z1 and Z2 are CR2;
Z3 is CH;
each R1 is independently and individually halogen, H, C1-C6 alkyl, branched C3-C7 alkyl, C3-C7 cycloalkyl, or —CN;

each R2 is individually and independently H, halogen, C1-C6 alkyl, or cyano;
R3 is —C(O)R4, —C(O)—C6-C10-aryl, —C(O)—C4-C6-heterocyclyl, or —C(O)—C5-C6-heteroaryl, wherein
aryl is phenyl, naphthyl, tetrahydronaphthyl, indenyl or indanyl; and
with the proviso that when R3 is —C(O)—C4-C6-heterocyclyl, the heterocyclyl does not have a N bonding hand to —C(O);
R4 is C3-C8 cycloalkyl, C1-C7 alkyl, —(CH$_2$)$_p$—CN, —(CH$_2$)$_p$—OR6, —(CH$_2$)$_p$—NR6(R7), —(CH$_2$)$_p$—SO$_2$—C1-C6-alkyl, —(CH$_2$)$_p$—C6-C10-aryl, —(CH$_2$)$_p$—C5-C6-heteroaryl, or —(CH$_2$)$_p$—C4-C6-heterocyclyl, wherein
each alkyl or alkylene is optionally substituted with one or two C1-C6 alkyl; and
aryl is phenyl, naphthyl, tetrahydronaphthyl, indenyl or indanyl;
each R6 and R7 is individually and independently H, C1-C6 alkyl, or C3-C8 branched alkyl;

each cycloalkyl, aryl, heteroaryl and heterocyclyl is independently substituted with —(R25)$_m$;

each R25 is individually and independently C1-C6 alkyl, branched C3-C8 alkyl, halogen, —(CH$_2$)$_m$—CN, —(CH$_2$)$_m$—OR6, —(CH$_2$)$_m$—NR6(R7), —(CH$_2$)$_m$—SO$_2$—C1-C6-alkyl, —(CH$_2$)$_m$—C(O)NR6(R7), —(CH$_2$)$_m$—C(O)—C4-C6-heterocyclyl, or —(CH$_2$)$_m$—C4-C6-heterocyclyl, wherein each alkyl or alkylene is optionally substituted with one or two C1-C6 alkyl;

each m is individually and independently 0, 1, 2, or 3; and p is 1, 2, or 3.

2. The compound of claim 1, wherein the compound is a compound of Formula Ic,

Formula Ic

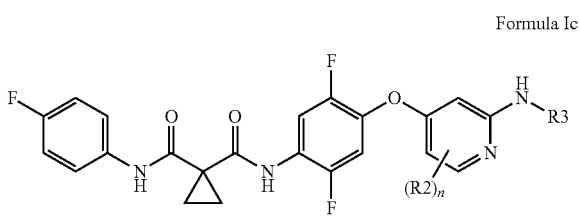

or a pharmaceutically acceptable salt, enantiomer, stereoisomer, or tautomer thereof, and wherein n is 0, 1, or 2.

3. The compound of claim 2, wherein R3 is —C(O)R4.

4. The compound of claim 3, wherein R4 is C3-C8 cycloalkyl, C1-C7 alkyl, —(CH$_2$)$_p$—CN, —(CH$_2$)$_p$—OR6, —(CH$_2$)$_p$—NR6(R7), —(CH$_2$)$_p$—SO$_2$—C1-C6-alkyl, or —(CH$_2$)$_p$—C4-C6-heterocyclyl, and wherein each alkyl or alkylene is optionally substituted with one or two C1-C6 alkyl.

5. The compound of claim 3, wherein R4 is C3-C8 cycloalkyl or C1-C7 alkyl, and wherein each alkyl or alkylene is optionally substituted with one or two C1-C6 alkyl.

6. The compound of claim 2, wherein R3 is —C(O)—C6-C10-aryl, —C(O)—C4-C6-heterocyclyl, or —C(O)—C5-C6-heteroaryl.

7. A compound of claim 1 selected from the group consisting of N-(4-(2-acetamidopyridin-4-yloxy)-2,5-difluorophenyl)-N'-(4-fluorophenyl)cyclopropane-1,1-dicarboxamide, N-(4-(2-acetamidopyridin-4-yloxy)-5-chloro-2-fluorophenyl)-N'-(4-fluorophenyl)cyclopropane-1,1-dicarboxamide, N-(4-(2-acetamidopyridin-4-yloxy)-2,5-difluorophenyl)-N'-phenylcyclopropane-1,1-dicarboxamide, N-(4-(2-(2-(dimethylamino)acetamido)pyridin-4-yloxy)-2,5-difluorophenyl)-N'-(4-fluorophenyl)cyclopropane-1,1- dicarboxamide, N-(4-(2-(cyclopropanecarboxamido)pyridin-4- yloxy)-2,5-difluorophenyl)-N'-(4-fluorophenyl) cyclopropane-1,1-dicarboxamide, N- (2, 5-difluoro-4-(2- propionamidopyridin-4-yloxy) phenyl)-N'-(4- fluorophenyl)cyclopropane-1,1-dicarboxamide, N-(2,5-difluoro-4-((2-(2-methoxyacetamido) pyridin- 4-yl)oxy)phenyl)-N'-(4-fluorophenyl) cyclopropane-1,1- dicarboxamide, N-(2,5-difluoro-4-(2- isobutyramidopyridin-4- yloxy)phenyl)-N'-(4-fluorophenyl)cyclopropane-1,1-dicarboxamide, N-(4-(2-(2-cyanoacetamido)pyridin-4-yloxy)-2,5-difluorophenyl)-N'-(4-fluorophenyl)cyclopropane-1,1-dicarboxamide, N-(4-(2-(azetidine-3-carboxamido)pyridin-4-yloxy)-2,5-difluorophenyl)-N'-(4-fluorophenyl)cyclopropane-1,1-dicarboxamide, N-(4-(2-(cyclobutanecarboxamido)pyridin-4-yloxy)-2,5-difluorophenyl)-N'-(4-fluorophenyl) cyclopropane-1,1-dicarboxamide, (R)—N-(2,5-difluoro-4-((2-(2-methoxypropanamido)pyridin-4-yl)oxy)phenyl)-N'-(4-fluorophenyl)cyclopropane-1,1-dicarboxamide, (R)—N-(2,5-difluoro-4-((2-(2-hydroxypropanamido)pyridin-4-yl)oxy)phenyl)-N'-(4-fluorophenyl)cyclopropane-1,1-dicarboxamide, N-(2,5-difluoro-4-((2-pivalamidopyridin-4-yl)oxy)phenyl)-N'-(4-fluorophenyl)cyclopropane-1,1-dicarboxamide, (S)—N-(2,5-difluoro-4-((2-(2-methoxypropanamido)pyridin-4-yl)oxy)phenyl)-N-(4-fluorophenyl)cyclopropane-1,1-dicarboxamide, (S)-1-((4-(2,5-difluoro-4-(1-((4-fluorophenyl) carbamoyl) cyclopropanecarboxamido)phenoxy)pyridin-2-yl)amino)-1-oxopropan-2-yl acetate, N-(2,5-difluoro-4-((2-(2-fluoro-2-methylpropanamido)pyridin-4-yl)oxy)phenyl)-N'-(4-fluorophenyl) cyclopropane-1,1- dicarboxamide and pharmaceutically acceptable salts and tautomers thereof.

8. A compound of claim 1 selected from N-(4-(2-(cyclopropanecarboxamido)pyridin-4-yloxy)-2,5-difluorophenyl)-N'-(4-fluorophenyl)cyclopropane-1,1-dicarboxamide, N-(2, 5-difluoro-4-(2-propionamidopyridin-4-yloxy)phenyl)-N'-(4-fluorophenyl)cyclopropane-1,1-dicarboxamide, N-(2,5-difluoro-4-(2-isobutyramidopyridin-4-yloxy)phenyl)-N'-(4-fluorophenyl)cyclopropane-1,1-dicarboxamide, N-(4-(2-acetamidopyridin-4-yloxy)-2,5-difluorophenyl)-N'-(4-fluorophenyl)cyclopropane-1,1-dicarboxamide.

9. A pharmaceutical composition, comprising a compound of claim 1 and a pharmaceutically acceptable carrier.

10. The composition of claim 9, further comprising an additive selected from adjuvants, excipients, diluents, or stabilizers.

11. The compound N-(4-(2-(cyclopropanecarboxamido) pyridin-4-yloxy)-2,5-difluorophenyl)-N'-(4-fluorophenyl) cyclopropane-1,1-dicarboxamide, or a pharmaceutically acceptable salt thereof.

12. A pharmaceutical composition, comprising the compound of claim 11 and a pharmaceutically acceptable carrier.

13. The composition of claim 12, further comprising an additive selected from adjuvants, excipients, diluents, or stabilizers.

14. The compound N-(2,5-difluoro-4-(2-propionamidopyridin-4-yloxy)phenyl)-N'-(4-fluorophenyl)cyclopropane-1, 1-dicarboxamide, or a pharmaceutically acceptable salt thereof.

15. A pharmaceutical composition, comprising the compound of claim 14 and a pharmaceutically acceptable carrier.

16. The composition of claim 15, further comprising an additive selected from adjuvants, excipients, diluents, or stabilizers.

17. The compound N-(4-(2-acetamidopyridin-4-yloxy)-2, 5-difluorophenyl)-N'-(4-fluorophenyl)cyclopropane-1,1-dicarboxamide, or a pharmaceutically acceptable salt, thereof.

18. A pharmaceutical composition, comprising the compound of claim 17 and a pharmaceutically acceptable carrier.

19. The composition of claim 18, further comprising an additive selected from adjuvants, excipients, diluents, or stabilizers.

\* \* \* \* \*

SEQUENCE LISTING

```
<160> NUMBER OF SEQ ID NOS: 4

<210> SEQ ID NO 1
<211> LENGTH: 676
<212> TYPE: PRT
<213> ORGANISM: Artificial Sequence
<220> FEATURE:
<223> OTHER INFORMATION: c-KIT with N-terminal GST fusion

<400> SEQUENCE: 1

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
```

-continued

```
                 85                  90                  95
Ile Arg Tyr Gly Val Ser Arg Ile Ala Tyr Ser Lys Asp Phe Glu Thr
            100                 105                 110
Leu Lys Val Asp Phe Leu Ser Lys Leu Pro Glu Met Leu Lys Met Phe
            115                 120                 125
Glu Asp Arg Leu Cys His Lys Thr Tyr Leu Asn Gly Asp His Val Thr
            130                 135                 140
His Pro Asp Phe Met Leu Tyr Asp Ala Leu Asp Val Val Leu Tyr Met
145                 150                 155                 160
Asp Pro Met Cys Leu Asp Ala Phe Pro Lys Leu Val Cys Phe Lys Lys
                165                 170                 175
Arg Ile Glu Ala Ile Pro Gln Ile Asp Lys Tyr Leu Lys Ser Ser Lys
            180                 185                 190
Tyr Ile Trp Pro Leu Gln Gly Trp Gln Ala Thr Phe Gly Gly Gly Asp
            195                 200                 205
His Pro Pro Lys Ser Asp Leu Val Pro Arg His Asn Gln Thr Ser Leu
            210                 215                 220
Tyr Lys Lys Ala Gly Ser Ala Ala Val Leu Glu Glu Asn Leu Tyr
225                 230                 235                 240
Phe Gln Gly Thr Tyr Lys Tyr Leu Gln Lys Pro Met Tyr Glu Val Gln
                245                 250                 255
Trp Lys Val Val Glu Glu Ile Asn Gly Asn Asn Tyr Val Tyr Ile Asp
            260                 265                 270
Pro Thr Gln Leu Pro Tyr Asp His Lys Trp Glu Phe Pro Arg Asn Arg
            275                 280                 285
Leu Ser Phe Gly Lys Thr Leu Gly Ala Gly Ala Phe Gly Lys Val Val
            290                 295                 300
Glu Ala Thr Ala Tyr Gly Leu Ile Lys Ser Asp Ala Ala Met Thr Val
305                 310                 315                 320
Ala Val Lys Met Leu Lys Pro Ser Ala His Leu Thr Glu Arg Glu Ala
                325                 330                 335
Leu Met Ser Glu Leu Lys Val Leu Ser Tyr Leu Gly Asn His Met Asn
            340                 345                 350
Ile Val Asn Leu Leu Gly Ala Cys Thr Ile Gly Gly Pro Thr Leu Val
            355                 360                 365
Ile Thr Glu Tyr Cys Cys Tyr Gly Asp Leu Leu Asn Phe Leu Arg Arg
            370                 375                 380
Lys Arg Asp Ser Phe Ile Cys Ser Lys Gln Glu Asp His Ala Glu Ala
385                 390                 395                 400
Ala Leu Tyr Lys Asn Leu Leu His Ser Lys Glu Ser Ser Cys Ser Asp
                405                 410                 415
Ser Thr Asn Glu Tyr Met Asp Met Lys Pro Gly Val Ser Tyr Val Val
            420                 425                 430
Pro Thr Lys Ala Asp Lys Arg Arg Ser Val Arg Ile Gly Ser Tyr Ile
            435                 440                 445
Glu Arg Asp Val Thr Pro Ala Ile Met Glu Asp Glu Leu Ala Leu
450                 455                 460
Asp Leu Glu Asp Leu Leu Ser Phe Ser Tyr Gln Val Ala Lys Gly Met
465                 470                 475                 480
Ala Phe Leu Ala Ser Lys Asn Cys Ile His Arg Asp Leu Ala Ala Arg
                485                 490                 495
Asn Ile Leu Leu Thr His Gly Arg Ile Thr Lys Ile Cys Asp Phe Gly
            500                 505                 510
```

```
Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
                580                 585                 590

Glu His Ala Pro Ala Glu Met Tyr Asp Ile Met Lys Thr Cys Trp Asp
            595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
                660                 665                 670

His Asp Asp Val
        675

<210> SEQ ID NO 2
<211> LENGTH: 474
<212> TYPE: PRT
<213> ORGANISM: Homo sapiens

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Ile Pro Phe Thr Met Lys Lys Arg Lys Gln Ile Lys Asp Leu
        35                  40                  45

Gly Ser Glu Leu Val Arg Tyr Asp Ala Arg Val His Thr Pro His Leu
    50                  55                  60

Asp Arg Leu Val Ser Ala Arg Ser Val Ser Pro Thr Thr Glu Met Val
65                  70                  75                  80

Ser Asn Glu Ser Val Asp Tyr Arg Ala Thr Phe Pro Glu Asp Gln Phe
                85                  90                  95

Pro Asn Ser Ser Gln Asn Gly Ser Cys Arg Gln Val Gln Tyr Pro Leu
            100                 105                 110

Thr Asp Met Ser Pro Ile Leu Thr Ser Gly Asp Ser Asp Ile Ser Ser
        115                 120                 125

Pro Leu Leu Gln Asn Thr Val His Ile Asp Leu Ser Ala Leu Asn Pro
    130                 135                 140

Glu Leu Val Gln Ala Val Gln His Val Val Ile Gly Pro Ser Ser Leu
145                 150                 155                 160

Ile Val His Phe Asn Glu Val Ile Gly Arg Gly His Phe Gly Cys Val
                165                 170                 175

Tyr His Gly Thr Leu Leu Asp Asn Asp Gly Lys Lys Ile His Cys Ala
            180                 185                 190

Val Lys Ser Leu Asn Arg Ile Thr Asp Ile Gly Glu Val Ser Gln Phe
        195                 200                 205
```

```
Leu Thr Glu Gly Ile Ile Met Lys Asp Phe Ser His Pro Asn Val Leu
            210                 215                 220

Ser Leu Leu Gly Ile Cys Leu Arg Ser Glu Gly Ser Pro Leu Val Val
225                 230                 235                 240

Leu Pro Tyr Met Lys His Gly Asp Leu Arg Asn Phe Ile Arg Asn Glu
                245                 250                 255

Thr His Asn Pro Thr Val Lys Asp Leu Ile Gly Phe Gly Leu Gln Val
                260                 265                 270

Ala Lys Gly Met Lys Tyr Leu Ala Ser Lys Lys Phe Val His Arg Asp
                275                 280                 285

Leu Ala Ala Arg Asn Cys Met Leu Asp Glu Lys Phe Thr Val Lys Val
            290                 295                 300

Ala Asp Phe Gly Leu Ala Arg Asp Met Tyr Asp Lys Glu Tyr Tyr Ser
305                 310                 315                 320

Val His Asn Lys Thr Gly Ala Lys Leu Pro Val Lys Trp Met Ala Leu
                325                 330                 335

Glu Ser Leu Gln Thr Gln Lys Phe Thr Thr Lys Ser Asp Val Trp Ser
                340                 345                 350

Phe Gly Val Leu Leu Trp Glu Leu Met Thr Arg Gly Ala Pro Pro Tyr
            355                 360                 365

Pro Asp Val Asn Thr Phe Asp Ile Thr Val Tyr Leu Leu Gln Gly Arg
            370                 375                 380

Arg Leu Leu Gln Pro Glu Tyr Cys Pro Asp Pro Leu Tyr Glu Val Met
385                 390                 395                 400

Leu Lys Cys Trp His Pro Lys Ala Glu Met Arg Pro Ser Phe Ser Glu
                405                 410                 415

Leu Val Ser Arg Ile Ser Ala Ile Phe Ser Thr Phe Ile Gly Glu His
                420                 425                 430

Tyr Val His Val Asn Ala Thr Tyr Val Asn Val Lys Cys Val Ala Pro
                435                 440                 445

Tyr Pro Ser Leu Leu Ser Ser Glu Asp Asn Ala Asp Asp Glu Val Asp
                450                 455                 460

Thr Arg Pro Ala Ser Phe Trp Glu Thr Ser
465                 470

<210> SEQ ID NO 3
<211> LENGTH: 315
<212> TYPE: PRT
<213> ORGANISM: Homo sapiens

<400> SEQUENCE: 3

Asp Pro Asp Glu Leu Pro Leu Asp Glu His Cys Glu Arg Leu Pro Tyr
1               5                   10                  15

Asp Ala Ser Lys Trp Glu Phe Pro Arg Asp Arg Leu Lys Leu Gly Lys
                20                  25                  30

Pro Leu Gly Arg Gly Ala Phe Gly Gln Val Ile Glu Ala Asp Ala Phe
            35                  40                  45

Gly Ile Asp Lys Thr Ala Thr Cys Arg Thr Val Ala Val Lys Met Leu
50                  55                  60

Lys Glu Gly Ala Thr His Ser Glu His Arg Ala Leu Met Ser Glu Leu
65                  70                  75                  80

Lys Ile Leu Ile His Ile Gly His His Leu Asn Val Val Asn Leu Leu
                85                  90                  95

Gly Ala Cys Thr Lys Pro Gly Gly Pro Leu Met Val Ile Val Glu Phe
                100                 105                 110
```

```
                                            -continued

Cys Lys Phe Gly Asn Leu Ser Thr Tyr Leu Arg Ser Lys Arg Asn Glu
        115                 120                 125

Phe Val Pro Tyr Lys Val Ala Pro Glu Asp Leu Tyr Lys Asp Phe Leu
    130                 135                 140

Thr Leu Glu His Leu Ile Cys Tyr Ser Phe Gln Val Ala Lys Gly Met
145                 150                 155                 160

Glu Phe Leu Ala Ser Arg Lys Cys Ile His Arg Asp Leu Ala Ala Arg
                165                 170                 175

Asn Ile Leu Leu Ser Glu Lys Asn Val Val Lys Ile Cys Asp Phe Gly
                180                 185                 190

Leu Ala Arg Asp Ile Tyr Lys Asp Pro Asp Tyr Val Arg Lys Gly Asp
            195                 200                 205

Ala Arg Leu Pro Leu Lys Trp Met Ala Pro Glu Thr Ile Phe Asp Arg
        210                 215                 220

Val Tyr Thr Ile Gln Ser Asp Val Trp Ser Phe Gly Val Leu Leu Trp
225                 230                 235                 240

Glu Ile Phe Ser Leu Gly Ala Ser Pro Tyr Pro Gly Val Lys Ile Asp
                245                 250                 255

Glu Glu Phe Cys Arg Arg Leu Lys Glu Gly Thr Arg Met Arg Ala Pro
            260                 265                 270

Asp Tyr Thr Thr Pro Glu Met Tyr Gln Thr Met Leu Asp Cys Trp His
        275                 280                 285

Gly Glu Pro Ser Gln Arg Pro Thr Phe Ser Glu Leu Val Glu His Leu
    290                 295                 300

Gly Asn Leu Leu Gln Ala Asn Ala Gln Gln Asp
305                 310                 315

<210> SEQ ID NO 4
<211> LENGTH: 13
<212> TYPE: PRT
<213> ORGANISM: Unknown
<220> FEATURE:
<223> OTHER INFORMATION: RON kinase peptide substrate

<400> SEQUENCE: 4

Lys Lys Ser Arg Gly Asp Tyr Met Thr Met Gln Ile Gly
1               5                   10
```